United States Patent [19]
Charon et al.

[11] Patent Number: 5,925,750
[45] Date of Patent: Jul. 20, 1999

[54] NUCLEIC ACID ENCODING POLYPEPTIDE OF A GROWTH FACTOR RECEPTOR FAMILY

[75] Inventors: Martine Charon; Sylvie Gisselbrecht; Jean-Francios Penciolelli; Michele Souyri, all of Paris; Pierre Tambourin, Gif-Sur-Yvette; Paule Varlet, Paris; Isabelle Vigon, Paris; Francoise Wendling, Paris, all of France

[73] Assignee: Institute National de la Sante et de la Recherche Medicale (INSERM), Paris, France

[21] Appl. No.: 08/078,311

[22] PCT Filed: Oct. 19, 1990

[86] PCT No.: PCT/FR90/00762

§ 371 Date: Jun. 18, 1993

§ 102(e) Date: Jun. 18, 1993

[87] PCT Pub. No.: WO92/07074

PCT Pub. Date: Apr. 30, 1992

[51] Int. Cl.$^6$ .......................... C12N 15/12; C07K 14/705
[52] U.S. Cl. ..................... 536/23.5; 530/350; 435/252.3; 435/254.11; 435/325; 435/348; 435/352; 435/365; 435/320.1

[56] References Cited

U.S. PATENT DOCUMENTS 5,580,753  12/1996  Yang et al. .............................. 435/69.5

OTHER PUBLICATIONS

Penciolelli et al., "Genetic Analysis of Myeloproliferative Leukemia Virus, a Novel Acute Leukemogenic Replication–Defective Retrovirus", *J. Virology,* 61:579–583 (1987).
Vigon et al., Oncogene, 8, 2607, 1993.
Wallace et al., Methods in Enzymology, 152, 432, 1987.
Bartley, R. T. et al., 1994, "Identification and cloning of a megakaryocyte growth and development factor that is a ligand for the cytokine receptor Mpl," Cell 77: 1117–1124.
Bénit, L. et al., 1994, "Characterization of mpl cytoplasmic domain sequences required for myeloproliferative leukemia virus pathogenicity," J. Virology 68:5270–5274.
Courtois, G. et al., 1995, "Constitutive activation of a variant of the env–mpl oncogene product by disulfide–linked homodimerization," J. Virology 69:2794–2800.
de Sauvage, F. et al., 1994, "Stimulation of megakaryocytopoiesis and thrombopoiesis by the c–Mpl ligand," Nature 369:533–538.
Le Coniat, M. et al., 1989, "The human homolog of the myeloproliferative virus maps to chromosome band 1p34," Hum. Genetics 83:194–196.
Methia, N. et al., 1993, "Oligodeoxynucleotides antisense to the proto–oncogene c–mpl specifically inhibit in vitro megakaryocytopoiesis," Blood 82:1395–1401.
Wendling, F. et al., 1994, "c–Mpl ligand is a humoral regulator of megakaryocytopoiesis," Nature 369:571–574.
Wendling, F. et al., 1990, "Myeloproliferative leukemia virus sustains proliferation and differentiation of hematopoietic progenitor cells," Exp. Hematol. 18:624.
Wendling, F. et al., 1989, "Myeloid progenitor cells transformed by the myeloproliferative leukemia virus proliferate and differentiate in vitro without the addition of growth factors," Leukemia 3:475–480.
Wendling, F. et al., 1989, "Factor–independent erythropoietic progenitor cells in leukemia induced by the myeloproliferative leukemia virus," Blood 73:1161–1167.
Wendling, F et al., 1986, "MPLV: a retrovirus complex inducing an acute myeloroliferative leukemic disorder in adult mice," Virology 149:242–246.
Benit et al., Oncogene, 8, 787, 1993.
Souyri et al., Cell, 63, 1137, 1990.
Vigon et al., PNAS, 89, 5640, 1992.
Skoda et al., EMBO, 12, 2645, 1993.

*Primary Examiner*—Sally P. Teng
*Attorney, Agent, or Firm*—Pennie & Edmonds LLP

[57] ABSTRACT

Polypeptide of a growth factor receptor family, having a specific sequence and presenting all or part of the following properties: it encourages and/or is involved in the proliferation and/or differentiation of hematopoietic cell lines when obtained from the MPLV retrovirus; it is capable of acting as a hematopoietic growth factor receptor; it is recognized by antibodies directed against it. Polypeptides similar to the above. Applications in the diagnosis of the expression of said ligand polypeptide.

17 Claims, 9 Drawing Sheets

|  |  |  |  |  |
|---|---|---|---|---|
| v-mpl | E L R - P R A R Y S L Q L R A R | L N G P T Y Q | G P W S A W S P P A |
| miL-3RI | K L F L P N S I Y A A R V R T R | L S A G S L S G | R P S R W S P E V |
| miL-3RII | Q L E - P D T S Y C A R V R V K | P I S D - Y D G | I W S E W S N E Y |
| mEPO R | N L R - G G T R Y T F A V R A R | M A E P S F S G | F W S A W S - E P |
| miL4R | I L M - S G V Y Y T A R V R V R | S Q I - - L T G | T W S E W S P S I |
| hIL2R | T L T - P D T Q Y E F Q V R V K | P L Q G E F - T | T W S P S Q P L |
| hIL6R | I H D - A W S G L R H V V Q L R | A Q E - E F C G | E W S E W S P E A |
| hIL7R | K L Q - P A A M Y E I K V R S | I P D H - Y F K G | F W S E W S P S Y |
| miL7R | K L R - P K A M Y E I K V R S | I P H H D Y F K G | F W S E W S P S S |
| consensus | L - - (P) - - - Y - R V R(V)R<br>K K | (F) - G - | W S(E)W S(P E) |

FIG.7

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 635 amino acids
      (B) TYPE: amino acid
      (D) TOPOLOGY: linear (ii) MOLECULE TYPE: peptide (xi) SEQUENCE DESCRIPTION: SEQ ID NO:1:

```
Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
            115                 120                 125

Ser Val Gly Leu Pro Ala Pro Pro Ser Ile Ile Lys Ala Met Gly Gly
        130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
            195                 200                 205

Ser Pro Cys Ala Gln Pro Thr Met Pro Trp Gln Asp Gly Pro Lys Gln
210                 215                 220
```

```
Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
            245                 250                 255

Arg Ser Glu Pro Asp Gly Ile Ser Leu Gly Gly Ser Trp Gly Ser Trp
                260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
                420                 425                 430

Gln Asp Trp Lys Val Leu Glu Pro Pro Leu Gly Ala Arg Gly Gly Thr
            435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
            515                 520                 525

Trp Pro Ser Leu Pro Asp Leu His Arg Val Leu Gly Gln Tyr Leu Arg
        530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
                580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
        610                 615                 620

Ser Tyr Leu Pro Leu Ser Tyr Trp Gln Gln Pro
625                 630                 635
```

(2) INFORMATION FOR SEQ ID NO:2:

(i) SEQUENCE CHARACTERISTICS:
        (A) LENGTH: 187 amino acids
        (B) TYPE: amino acid
        (D) TOPOLOGY: linear (ii) MOLECULE TYPE: peptide (xi) SEQUENCE DESCRIPTION: SEQ ID NO:2:

```
Leu Glu Leu Arg Pro Arg Ser Arg Tyr Arg Leu Gln Leu Arg Ala Arg
1               5                   10                  15

Leu Asn Gly Pro Thr Tyr Gln Gly Pro Trp Ser Ser Trp Ser Asp Pro
            20                  25                  30

Thr Arg Val Glu Thr Ala Thr Glu Thr Ala Trp Ile Ser Leu Val Thr
            35                  40                  45

Ala Leu His Leu Val Leu Gly Leu Ser Ala Val Leu Gly Leu Leu Leu
        50                  55                  60

Leu Arg Trp Gln Phe Pro Ala His Tyr Arg Arg Leu Arg His Ala Leu
65                  70                  75                  80

Trp Pro Ser Leu Pro Asp Leu His Arg Val Leu Gly Gln Tyr Leu Arg
                85                  90                  95

Asp Thr Ala Ala Leu Ser Pro Pro Lys Ala Thr Val Ser Asp Thr Cys
            100                 105                 110

Glu Glu Val Glu Pro Ser Leu Leu Glu Ile Leu Pro Lys Ser Ser Glu
            115                 120                 125

Arg Thr Pro Leu Pro Leu Cys Ser Ser Gln Ala Gln Met Asp Tyr Arg
        130                 135                 140

Arg Leu Gln Pro Ser Cys Leu Gly Thr Met Pro Leu Ser Val Cys Pro
145                 150                 155                 160

Pro Met Ala Glu Ser Gly Ser Cys Cys Thr Thr His Ile Ala Asn His
                165                 170                 175

Ser Tyr Leu Pro Leu Ser Tyr Trp Gln Gln Pro
            180                 185
```

(2) INFORMATION FOR SEQ ID NO:3:

(i) SEQUENCE CHARACTERISTICS:
        (A) LENGTH: 382 amino acids
        (B) TYPE: amino acid
        (D) TOPOLOGY: linear (ii) MOLECULE TYPE: peptide (xi) SEQUENCE DESCRIPTION: SEQ ID NO:3:

```
Ile Leu Leu Leu Ser Tyr Ala Ala Asn Arg Arg Gly Leu Pro Ser Trp
1               5                   10                  15

Leu Leu Gly Pro Trp Ser Phe Pro Val Thr Val Asp Leu Pro Gly Asp
            20                  25                  30

Ala Val Thr Ile Gly Leu Gln Cys Phe Thr Leu Asp Leu Lys Met Val
            35                  40                  45

Thr Cys Gln Trp Gln Gln Gln Asp Arg Thr Ser Ser Gln Gly Phe Phe
    50                  55                  60

Arg His Ser Arg Thr Arg Cys Cys Pro Thr Asp Arg Asp Pro Thr Trp
65                  70                  75                  80

Glu Lys Cys Glu Glu Glu Glu Pro Arg Pro Gly Ser Gln Pro Ala Leu
                85                  90                  95

Val Ser Arg Cys His Phe Lys Ser Arg Asn Asp Ser Val Ile His Ile
            100                 105                 110
```

```
Leu Val Glu Val Thr Thr Ala Gln Gly Ala Val His Ser Tyr Leu Gly
        115                 120                 125

Ser Pro Phe Trp Ile His Gln Ala Val Leu Leu Pro Thr Pro Ser Leu
        130                 135                 140

His Trp Arg Glu Val Ser Gly Arg Leu Glu Leu Glu Trp Gln His
145             150                 155                 160

Gln Ser Ser Trp Ala Ala Gln Glu Thr Cys Tyr Gln Leu Arg Tyr Thr
                165                 170                 175

Gly Glu Gly Arg Glu Asp Trp Lys Val Leu Glu Pro Ser Leu Gly Ala
                180                 185                 190

Arg Gly Gly Thr Leu Glu Leu Arg Pro Arg Ala Arg Tyr Ser Leu Gln
        195                 200                 205

Leu Arg Ala Arg Leu Asn Gly Pro Thr Tyr Gln Gly Pro Trp Ser Ala
        210                 215                 220

Trp Ser Pro Pro Ala Arg Val Ser Thr Gly Ser Glu Thr Ala Trp Ile
225                 230                 235                 240

Thr Leu Val Thr Ala Leu Leu Val Leu Ser Leu Ala Leu Leu
                245                 250                 255

Gly Leu Leu Leu Lys Trp Gln Phe Pro Ala His Tyr Arg Arg Leu
                260                 265                 270

Arg His Ala Leu Trp Pro Ser Leu Pro Asp Leu His Arg Val Leu Gly
        275                 280                 285

Gln Tyr Leu Arg Asp Thr Ala Ala Leu Ser Pro Ser Lys Ala Thr Val
        290                 295                 300

Thr Asp Ser Cys Glu Glu Val Glu Pro Ser Leu Leu Glu Ile Leu Pro
305                 310                 315                 320

Lys Ser Ser Glu Ser Thr Pro Leu Pro Leu Cys Pro Ser Gln Pro Gln
                325                 330                 335

Met Asp Tyr Arg Gly Leu Gln Pro Cys Leu Arg Thr Met Pro Leu Ser
                340                 345                 350

Val Cys Pro Pro Met Ala Glu Thr Gly Ser Cys Cys Thr Thr His Ile
        355                 360                 365

Ala Asn His Ser Tyr Leu Pro Leu Ser Tyr Trp Gln Gln Pro
        370                 375                 380

(2) INFORMATION FOR SEQ ID NO:4:

(i) SEQUENCE CHARACTERISTICS:
        (A) LENGTH: 184 amino acids
        (B) TYPE: amino acid
        (D) TOPOLOGY: linear (ii) MOLECULE TYPE: peptide (xi) SEQUENCE DESCRIPTION: SEQ ID NO:4:

Leu Glu Leu Arg Pro Arg Ala Arg Tyr Ser Leu Gln Leu Arg Ala Arg
1               5                   10                  15

Leu Asn Gly Pro Thr Tyr Gln Gly Pro Trp Ser Ala Trp Ser Pro Pro
                20                  25                  30

Ala Arg Val Ser Thr Gly Ser Glu Thr Ala Trp Ile Thr Leu Val Thr
                35                  40                  45

Ala Leu Leu Leu Val Leu Ser Leu Ser Ala Leu Leu Gly Leu Leu Leu
        50                  55                  60

Leu Lys Trp Gln Phe Pro Ala His Tyr Arg Arg Leu Arg His Ala Leu
65                  70                  75                  80

Trp Pro Ser Leu Pro Asp Leu His Arg Val Leu Gly Gln Tyr Leu Arg
                85                  90                  95
```

```
Asp Thr Ala Ala Leu Ser Pro Ser Lys Ala Thr Val Thr Asp Ser Cys
            100                 105                 110

Glu Glu Val Glu Pro Ser Leu Leu Glu Ile Leu Pro Lys Ser Ser Glu
        115                 120                 125

Ser Thr Pro Leu Pro Leu Cys Pro Ser Gln Pro Gln Met Asp Tyr Arg
    130                 135                 140

Gly Leu Gln Pro Cys Leu Arg Thr Met Pro Leu Ser Val Cys Pro Pro
145                 150                 155                 160

Met Ala Glu Thr Gly Ser Cys Cys Thr Thr His Ile Ala Asn His Ser
                165                 170                 175

Tyr Leu Pro Leu Ser Tyr Trp Gln
            180
```

(2) INFORMATION FOR SEQ ID NO:5:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:5:

```
Trp Gln Phe Pro Ala His Tyr Arg Arg Leu Arg His Ala Leu Trp Pro
1               5                   10                  15

Ser Leu Pro Asp Leu His Arg Val Leu Gly Gln Tyr Leu Arg Asp Thr
            20                  25                  30

Ala Ala Leu Ser Pro
            35
```

(2) INFORMATION FOR SEQ ID NO:6:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:6:

```
Leu Val Thr Ala Leu His Leu Val Leu Gly Leu Ser Ala Val Leu Gly
1               5                   10                  15

Leu Leu Leu Leu
            20
```

(2) INFORMATION FOR SEQ ID NO:7:

(i) SEQUENCE CHARACTERISTICS:
        (A) LENGTH: 493 amino acids
        (B) TYPE: amino acid
        (D) TOPOLOGY: linear (ii) MOLECULE TYPE: peptide (xi) SEQUENCE DESCRIPTION: SEQ ID NO:7:

```
Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
```

-continued

```
              50                  55                  60
Leu Leu Tyr Ala Tyr Pro Arg Glu Lys Pro Arg Ala Cys Pro Leu Ser
 65                  70                  75                  80

Ser Gln Ser Met Pro His Phe Gly Thr Arg Tyr Val Cys Gln Phe Pro
                 85                  90                  95

Asp Gln Glu Glu Val Arg Leu Phe Phe Pro Leu His Leu Trp Val Lys
                100                 105                 110

Asn Val Phe Leu Asn Gln Thr Arg Thr Gln Arg Val Leu Phe Val Asp
                115                 120                 125

Ser Val Gly Leu Pro Ala Pro Pro Ser Ile Ile Lys Ala Met Gly Gly
130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
                180                 185                 190

Cys Cys Pro Ala Leu Gln Arg Pro His Ser Ala Ser Ala Leu Asp Gln
                195                 200                 205

Ser Pro Cys Ala Gln Pro Thr Met Pro Trp Gln Asp Gly Pro Lys Gln
210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
                260                 265                 270

Ser Leu Pro Val Thr Val Asp Leu Pro Gly Asp Ala Val Ala Leu Gly
                275                 280                 285

Leu Gln Cys Phe Thr Leu Asp Leu Lys Asn Val Thr Cys Gln Trp Gln
290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
                340                 345                 350

His Phe Lys Ser Arg Asn Asp Ser Ile Ile His Ile Leu Val Glu Val
                355                 360                 365

Thr Thr Ala Pro Gly Thr Val His Ser Tyr Leu Gly Ser Pro Phe Trp
                370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
                420                 425                 430

Gln Asp Trp Lys Val Leu Glu Pro Pro Leu Gly Ala Arg Gly Gly Thr
                435                 440                 445

Leu Glu Leu Arg Pro Arg Ser Arg Tyr Arg Leu Gln Leu Arg Ala Arg
                450                 455                 460

Leu Asn Gly Pro Thr Tyr Gln Gly Pro Trp Ser Ser Trp Ser Asp Pro
465                 470                 475                 480
```

```
Thr Arg Val Glu Thr Ala Thr Glu Thr Ala Trp Ile Ser
            485                 490
```

(2) INFORMATION FOR SEQ ID NO:8:

(i) SEQUENCE CHARACTERISTICS:
        (A) LENGTH: 122 amino acids
        (B) TYPE: amino acid
        (D) TOPOLOGY: linear (ii) MOLECULE TYPE: peptide (xi) SEQUENCE DESCRIPTION: SEQ ID NO:8:

```
Arg Trp Gln Phe Pro Ala His Tyr Arg Arg Leu Arg His Ala Leu Trp
1               5                   10                  15
Pro Ser Leu Pro Asp Leu His Arg Val Leu Gly Gln Tyr Leu Arg Asp
            20                  25                  30
Thr Ala Ala Leu Ser Pro Pro Lys Ala Thr Val Ser Asp Thr Cys Glu
        35                  40                  45
Glu Val Glu Pro Ser Leu Leu Glu Ile Leu Pro Lys Ser Ser Glu Arg
    50                  55                  60
Thr Pro Leu Pro Leu Cys Ser Ser Gln Ala Gln Met Asp Tyr Arg Arg
65                  70                  75                  80
Leu Gln Pro Ser Cys Leu Gly Thr Met Pro Leu Ser Val Cys Pro Pro
                85                  90                  95
Met Ala Glu Ser Gly Ser Cys Cys Thr Thr His Ile Ala Asn His Ser
            100                 105                 110
Tyr Leu Pro Leu Ser Tyr Trp Gln Gln Pro
            115                 120
```

(2) INFORMATION FOR SEQ ID NO:9:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:9:

```
Leu Val Thr Ala Leu Leu Val Leu Ser Leu Ser Ala Leu Leu Gly
1               5                   10                  15
Leu Leu Leu Leu
            20
```

(2) INFORMATION FOR SEQ ID NO:10:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:10:

```
Leu Glu Leu Arg Pro Arg Ala Arg Tyr Ser Leu Gln Leu Arg Ala Arg
1               5                   10                  15
Leu Asn Gly Pro Thr Tyr Gln Gly Pro Trp Ser Ala Trp Ser Pro Pro
            20                  25                  30
Ala Arg Val Ser Thr Gly Ser Glu Thr Ala Trp Ile Thr
        35                  40                  45
```

(2) INFORMATION FOR SEQ ID NO:11:

(i) SEQUENCE CHARACTERISTICS:
    (A) LENGTH: 119 amino acids
    (B) TYPE: amino acid
    (D) TOPOLOGY: linear (ii) MOLECULE TYPE: peptide (xi) SEQUENCE DESCRIPTION: SEQ ID NO:11:

```
Lys Trp Gln Phe Pro Ala His Tyr Arg Arg Leu Arg His Ala Leu Trp
1               5                   10                  15

Pro Ser Leu Pro Asp Leu His Arg Val Leu Gly Gln Tyr Leu Arg Asp
            20                  25                  30

Thr Ala Ala Leu Ser Pro Ser Lys Ala Thr Val Thr Asp Ser Cys Glu
            35                  40                  45

Glu Val Glu Pro Ser Leu Leu Glu Ile Leu Pro Lys Ser Ser Glu Ser
        50                  55                  60

Thr Pro Leu Pro Leu Cys Pro Ser Gln Pro Gln Met Asp Tyr Arg Gly
65                  70                  75                  80

Leu Gln Pro Cys Leu Arg Thr Met Pro Leu Ser Val Cys Pro Pro Met
                85                  90                  95

Ala Glu Thr Gly Ser Cys Cys Thr Thr His Ile Ala Asn His Ser Tyr
            100                 105                 110

Leu Pro Leu Ser Tyr Trp Gln
            115
```

(2) INFORMATION FOR SEQ ID NO:12:

(i) SEQUENCE CHARACTERISTICS:
    (A) LENGTH: 448 amino acids
    (B) TYPE: amino acid
    (D) TOPOLOGY: linear (ii) MOLECULE TYPE: peptide (xi) SEQUENCE DESCRIPTION: SEQ ID NO:12:

```
Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
            35                  40                  45

Thr Cys Phe Trp Asp Glu Glu Ala Ala Pro Ser Gly Thr Tyr Gln
        50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
            115                 120                 125

Ser Val Gly Leu Pro Ala Pro Pro Ser Ile Ile Lys Ala Met Gly Gly
    130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
```

```
                180              185              190
Cys Cys Pro Ala Leu Gln Arg Pro His Ser Ala Ser Ala Leu Asp Gln
        195              200              205

Ser Pro Cys Ala Gln Pro Thr Met Pro Trp Gln Asp Gly Pro Lys Gln
    210              215              220

Thr Ser Pro Ser Arg Glu Ala Ser Ala Leu Thr Ala Glu Gly Gly Ser
225              230              235              240

Cys Leu Ile Ser Gly Leu Gln Pro Gly Asn Ser Tyr Trp Leu Gln Leu
            245              250              255

Arg Ser Glu Pro Asp Gly Ile Ser Leu Gly Gly Ser Trp Gly Ser Trp
                260              265              270

Ser Leu Pro Val Thr Val Asp Leu Pro Gly Asp Ala Val Ala Leu Gly
        275              280              285

Leu Gln Cys Phe Thr Leu Asp Leu Lys Asn Val Thr Cys Gln Trp Gln
    290              295              300

Gln Gln Asp His Ala Ser Ser Gln Gly Phe Phe Tyr His Ser Arg Ala
305              310              315              320

Arg Cys Cys Pro Arg Asp Arg Tyr Pro Ile Trp Glu Asn Cys Glu Glu
            325              330              335

Glu Glu Lys Thr Asn Pro Gly Leu Gln Thr Pro Gln Phe Ser Arg Cys
                340              345              350

His Phe Lys Ser Arg Asn Asp Ser Ile Ile His Ile Leu Val Glu Val
        355              360              365

Thr Thr Ala Pro Gly Thr Val His Ser Tyr Leu Gly Ser Pro Phe Trp
    370              375              380

Ile His Gln Ala Val Arg Leu Pro Thr Pro Asn Leu His Trp Arg Glu
385              390              395              400

Ile Ser Ser Gly His Leu Glu Leu Glu Trp Gln His Pro Ser Ser Trp
            405              410              415

Ala Ala Gln Glu Thr Cys Tyr Gln Leu Arg Tyr Thr Gly Glu Gly His
                420              425              430

Gln Asp Trp Lys Val Leu Glu Pro Pro Leu Gly Ala Arg Gly Gly Thr
        435              440              445

(2) INFORMATION FOR SEQ ID NO:13:

(i) SEQUENCE CHARACTERISTICS:
        (A) LENGTH: 196 amino acids
        (B) TYPE: amino acid
        (D) TOPOLOGY: linear (ii) MOLECULE TYPE: peptide (xi) SEQUENCE DESCRIPTION: SEQ ID NO:13:

Ile Leu Leu Leu Ser Tyr Ala Ala Asn Arg Arg Gly Leu Pro Ser Trp
1               5               10              15

Leu Leu Gly Pro Trp Ser Phe Pro Val Thr Val Asp Leu Pro Gly Glu
            20              25              30

Ala Val Ile Ile Gly Leu Gln Cys Phe Thr Leu Asp Leu Lys Met Val
                35              40              45

Thr Cys Gln Trp Gln Gln Gln Asp Arg Thr Ser Ser Gln Gly Phe Phe
    50              55              60

Arg His Ser Arg Thr Arg Cys Cys Pro Thr Asp Arg Asp Pro Thr Trp
65              70              75              80

Glu Lys Cys Glu Glu Glu Glu Pro Arg Pro Gly Ser Gln Pro Ala Leu
            85              90              95
```

```
Val Ser Arg Cys His Phe Lys Ser Arg Asn Asp Ser Val Ile His Ile
            100                 105                 110

Leu Val Glu Val Thr Thr Ala Gln Gly Ala Val His Ser Tyr Leu Gly
            115                 120                 125

Ser Pro Phe Trp Ile His Gln Ala Val Leu Leu Pro Thr Pro Ser Leu
            130                 135                 140

His Trp Arg Glu Val Ser Ser Gly Arg Leu Glu Leu Glu Trp Gln His
145                 150                 155                 160

Gln Ser Ser Trp Ala Ala Gln Glu Thr Cys Tyr Gln Leu Arg Tyr Thr
                165                 170                 175

Gly Glu Gly Arg Glu Asp Trp Lys Val Leu Glu Pro Ser Leu Gly Ala
                180                 185                 190

Arg Gly Gly Thr
            195

(2) INFORMATION FOR SEQ ID NO:14:

(i) SEQUENCE CHARACTERISTICS:
        (A) LENGTH: 284 amino acids
        (B) TYPE: amino acid
        (D) TOPOLOGY: linear (ii) MOLECULE TYPE: peptide (xi) SEQUENCE DESCRIPTION: SEQ ID NO:14:

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
                20                  25                  30

Arg Ser Ala Ala Pro Gly Ser Ser Pro His Gln Val Tyr Asn Ile Thr
            35                  40                  45

Trp Glu Val Thr Asn Gly Asp Arg Glu Thr Val Trp Ala Ile Ser Gly
50                  55                  60

Arg Leu Tyr Val Ser Gly Arg Asp Pro Gly Leu Thr Phe Gly Ile Arg
65                  70                  75                  80

Leu Arg Tyr Gln Asn Leu Gly Pro Arg Val Pro Ile Gly Pro Asn Pro
                85                  90                  95

Val Leu Ala Asp Leu Glu Leu Arg Pro Arg Ala Arg Tyr Ser Leu Gln
            100                 105                 110

Leu Arg Ala Arg Leu Asn Gly Pro Thr Tyr Gln Gly Pro Trp Ser Ala
            115                 120                 125

Trp Ser Pro Pro Ala Arg Val Ser Thr Gly Ser Glu Thr Ala Trp Ile
            130                 135                 140

Thr Leu Val Thr Ala Leu Leu Leu Val Leu Ser Leu Ser Ala Leu Leu
145                 150                 155                 160

Gly Leu Leu Leu Leu Lys Trp Gln Phe Pro Ala His Tyr Arg Arg Leu
                165                 170                 175

Arg His Ala Leu Trp Pro Ser Leu Pro Asp Leu His Arg Val Leu Gly
            180                 185                 190

Gln Tyr Leu Arg Asp Thr Ala Ala Leu Ser Pro Ser Lys Ala Thr Val
            195                 200                 205

Thr Asp Ser Cys Glu Glu Val Glu Pro Ser Leu Leu Glu Ile Leu Pro
            210                 215                 220

Lys Ser Ser Glu Ser Thr Pro Leu Pro Leu Cys Pro Ser Gln Pro Gln
225                 230                 235                 240

Met Asp Tyr Arg Gly Leu Gln Pro Cys Leu Arg Thr Met Pro Leu Ser
                245                 250                 255
```

```
Val Cys Pro Pro Met Ala Glu Thr Gly Ser Cys Cys Thr Thr His Ile
            260                 265                 270

Ala Asn His Ser Tyr Leu Pro Leu Ser Tyr Trp Gln
            275                 280

(2) INFORMATION FOR SEQ ID NO:15:

(i) SEQUENCE CHARACTERISTICS:
        (A) LENGTH: 2034 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 4..1908

(xi) SEQUENCE DESCRIPTION: SEQ ID NO:15:

AAG ATG CCC TCC TGG GCC CTC TTC ATG GTC ACC TCC TGC CTC CTC CTG          48
    Met Pro Ser Trp Ala Leu Phe Met Val Thr Ser Cys Leu Leu Leu
    1               5                   10                  15

GCC CCT CAA AAC CTG GCC CAA GTC AGC AGC CAA GAT GTC TCC TTG CTG          96
Ala Pro Gln Asn Leu Ala Gln Val Ser Ser Gln Asp Val Ser Leu Leu
                20                  25                  30

GCA TCA GAC TCA GAG CCC CTG AAG TGT TTC TCC CGA ACA TTT GAG GAC         144
Ala Ser Asp Ser Glu Pro Leu Lys Cys Phe Ser Arg Thr Phe Glu Asp
            35                  40                  45

CTC ACT TGC TTC TGG GAT GAG GAA GAG GCA GCG CCC AGT GGG ACA TAC         192
Leu Thr Cys Phe Trp Asp Glu Glu Glu Ala Ala Pro Ser Gly Thr Tyr
        50                  55                  60

CAG CTG CTG TAT GCC TAC CCG CGG GAG AAG CCC CGT GCT TGC CCC CTG         240
Gln Leu Leu Tyr Ala Tyr Pro Arg Glu Lys Pro Arg Ala Cys Pro Leu
    65                  70                  75

AGT TCC CAG AGC ATG CCC CAC TTT GGA ACC CGA TAC GTG TGC CAG TTT         288
Ser Ser Gln Ser Met Pro His Phe Gly Thr Arg Tyr Val Cys Gln Phe
80                  85                  90                  95

CCA GAC CAG GAG GAA GTG CGT CTC TTC TTT CCG CTG CAC CTC TGG GTG         336
Pro Asp Gln Glu Glu Val Arg Leu Phe Phe Pro Leu His Leu Trp Val
                100                 105                 110

AAG AAT GTG TTC CTA AAC CAG ACT CGG ACT CAG CGA GTC CTC TTT GTG         384
Lys Asn Val Phe Leu Asn Gln Thr Arg Thr Gln Arg Val Leu Phe Val
            115                 120                 125

GAC AGT GTA GGC CTG CCG GCT CCC CCC AGT ATC ATC AAG GCC ATG GGT         432
Asp Ser Val Gly Leu Pro Ala Pro Pro Ser Ile Ile Lys Ala Met Gly
        130                 135                 140

GGG AGC CAG CCA GGG GAA CTT CAG ATC AGC TGG GAG GAG CCA GCT CCA         480
Gly Ser Gln Pro Gly Glu Leu Gln Ile Ser Trp Glu Glu Pro Ala Pro
    145                 150                 155

GAA ATC AGT GAT TTC CTG AGG TAC GAA CTC CGC TAT GGC CCC AGA GAT         528
Glu Ile Ser Asp Phe Leu Arg Tyr Glu Leu Arg Tyr Gly Pro Arg Asp
160                 165                 170                 175

CCC AAG AAC TCC ACT GGT CCC ACG GTC ATA CAG CTG ATT GCC ACA GAA         576
Pro Lys Asn Ser Thr Gly Pro Thr Val Ile Gln Leu Ile Ala Thr Glu
                180                 185                 190

ACC TGC TGC CCT GCT CTG CAG AGG CCT CAC TCA GCC TCT GCT CTG GAC         624
Thr Cys Cys Pro Ala Leu Gln Arg Pro His Ser Ala Ser Ala Leu Asp
            195                 200                 205

CAG TCT CCA TGT GCT CAG CCC ACA ATG CCC TGG CAA GAT GGA CCA AAG         672
Gln Ser Pro Cys Ala Gln Pro Thr Met Pro Trp Gln Asp Gly Pro Lys
        210                 215                 220
```

-continued

| | |
|---|---|
| CAG ACC TCC CCA AGT AGA GAA GCT TCA GCT CTG ACA GCA GAG GGT GGA<br>Gln Thr Ser Pro Ser Arg Glu Ala Ser Ala Leu Thr Ala Glu Gly Gly<br>225 230 235 | 720 |
| AGC TGC CTC ATC TCA GGA CTC CAG CCT GGC AAC TCC TAC TGG CTG CAG<br>Ser Cys Leu Ile Ser Gly Leu Gln Pro Gly Asn Ser Tyr Trp Leu Gln<br>240 245 250 255 | 768 |
| CTG CGC AGC GAA CCT GAT GGG ATC TCC CTC GGT GGC TCC TGG GGA TCC<br>Leu Arg Ser Glu Pro Asp Gly Ile Ser Leu Gly Gly Ser Trp Gly Ser<br>260 265 270 | 816 |
| TGG TCC CTC CCT GTG ACT GTG GAC CTG CCT GGA GAT GCA GTG GCA CTT<br>Trp Ser Leu Pro Val Thr Val Asp Leu Pro Gly Asp Ala Val Ala Leu<br>275 280 285 | 864 |
| GGA CTG CAA TGC TTT ACC TTG GAC CTG AAG AAT GTT ACC TGT CAA TGG<br>Gly Leu Gln Cys Phe Thr Leu Asp Leu Lys Asn Val Thr Cys Gln Trp<br>290 295 300 | 912 |
| CAG CAA CAG GAC CAT GCT AGC TCC CAA GGC TTC TTC TAC CAC AGC AGG<br>Gln Gln Gln Asp His Ala Ser Ser Gln Gly Phe Phe Tyr His Ser Arg<br>305 310 315 | 960 |
| GCA CGG TGC TGC CCC AGA GAC AGG TAC CCC ATC TGG GAG AAC TGC GAA<br>Ala Arg Cys Cys Pro Arg Asp Arg Tyr Pro Ile Trp Glu Asn Cys Glu<br>320 325 330 335 | 1008 |
| GAG GAA GAG AAA ACA AAT CCA GGA CTA CAG ACC CCA CAG TTC TCT CGC<br>Glu Glu Glu Lys Thr Asn Pro Gly Leu Gln Thr Pro Gln Phe Ser Arg<br>340 345 350 | 1056 |
| TGC CAC TTC AAG TCA CGA AAT GAC AGC ATT ATT CAC ATC CTT GTG GAG<br>Cys His Phe Lys Ser Arg Asn Asp Ser Ile Ile His Ile Leu Val Glu<br>355 360 365 | 1104 |
| GTG ACC ACA GCC CCG GGT ACT GTT CAC AGC TAC CTG GGC TCC CCT TTC<br>Val Thr Thr Ala Pro Gly Thr Val His Ser Tyr Leu Gly Ser Pro Phe<br>370 375 380 | 1152 |
| TGG ATC CAC CAG GCT GTG CGC CTC CCC ACC CCA AAC TTG CAC TGG AGG<br>Trp Ile His Gln Ala Val Arg Leu Pro Thr Pro Asn Leu His Trp Arg<br>385 390 395 | 1200 |
| GAG ATC TCC AGT GGG CAT CTG GAA TTG GAG TGG CAG CAC CCA TCG TCC<br>Glu Ile Ser Ser Gly His Leu Glu Leu Glu Trp Gln His Pro Ser Ser<br>400 405 410 415 | 1248 |
| TGG GCA GCC CAA GAG ACC TGT TAT CAA CTC CGA TAC ACA GGA GAA GGC<br>Trp Ala Ala Gln Glu Thr Cys Tyr Gln Leu Arg Tyr Thr Gly Glu Gly<br>420 425 430 | 1296 |
| CAT CAG GAC TGG AAG GTG CTG GAG CCG CCT CTC GGG GCC CGA GGA GGG<br>His Gln Asp Trp Lys Val Leu Glu Pro Pro Leu Gly Ala Arg Gly Gly<br>435 440 445 | 1344 |
| ACC CTG GAG CTG CGC CCG CGA TCT CGC TAC CGT TTA CAG CTG CGC GCC<br>Thr Leu Glu Leu Arg Pro Arg Ser Arg Tyr Arg Leu Gln Leu Arg Ala<br>450 455 460 | 1392 |
| AGG CTC AAC GGC CCC ACC TAC CAA GGT CCC TGG AGC TCG TGG TCG GAC<br>Arg Leu Asn Gly Pro Thr Tyr Gln Gly Pro Trp Ser Ser Trp Ser Asp<br>465 470 475 | 1440 |
| CCA ACT AGG GTG GAG ACC GCC ACC GAG ACC GCC TGG ATC TCC TTG GTG<br>Pro Thr Arg Val Glu Thr Ala Thr Glu Thr Ala Trp Ile Ser Leu Val<br>480 485 490 495 | 1488 |
| ACC GCT CTG CAT CTA GTG CTG GGC CTC AGC GCC GTC CTG GGC CTG CTG<br>Thr Ala Leu His Leu Val Leu Gly Leu Ser Ala Val Leu Gly Leu Leu<br>500 505 510 | 1536 |
| CTG CTG AGG TGG CAG TTT CCT GCA CAC TAC AGG AGA CTG AGG CAT GCC<br>Leu Leu Arg Trp Gln Phe Pro Ala His Tyr Arg Arg Leu Arg His Ala<br>515 520 525 | 1584 |
| CTG TGG CCC TCA CTT CCA GAC CTG CAC CGG GTC CTA GGC CAG TAC CTT<br>Leu Trp Pro Ser Leu Pro Asp Leu His Arg Val Leu Gly Gln Tyr Leu<br>530 535 540 | 1632 |

-continued

| | | |
|---|---|---|
| AGG GAC ACT GCA GCC CTG AGC CCG CCC AAG GCC ACA GTC TCA GAT ACC<br>Arg Asp Thr Ala Ala Leu Ser Pro Pro Lys Ala Thr Val Ser Asp Thr<br>545                                550                              555 | 1680 |
| TGT GAA GAA GTG GAA CCC AGC CTC CTT GAA ATC CTC CCC AAG TCC TCA<br>Cys Glu Glu Val Glu Pro Ser Leu Leu Glu Ile Leu Pro Lys Ser Ser<br>560                              565                        570                      575 | 1728 |
| GAG AGG ACT CCT TTG CCC CTG TGT TCC TCC CAG GCC CAG ATG GAC TAC<br>Glu Arg Thr Pro Leu Pro Leu Cys Ser Ser Gln Ala Gln Met Asp Tyr<br>                            580                        585                        590 | 1776 |
| CGA AGA TTG CAG CCT TCT TGC CTG GGG ACC ATG CCC CTG TCT GTG TGC<br>Arg Arg Leu Gln Pro Ser Cys Leu Gly Thr Met Pro Leu Ser Val Cys<br>            595                        600                        605 | 1824 |
| CCA CCC ATG GCT GAG TCA GGG TCC TGC TGT ACC ACC CAC ATT GCC AAC<br>Pro Pro Met Ala Glu Ser Gly Ser Cys Cys Thr Thr His Ile Ala Asn<br>610                              615                        620 | 1872 |
| CAT TCC TAC CTA CCA CTA AGC TAT TGG CAG CAG CCT TGAGGACAGG<br>His Ser Tyr Leu Pro Leu Ser Tyr Trp Gln Gln Pro<br>625                              630                        635 | 1918 |
| CTCCTCACTC CCAGTTCCCT GGACAGAGCT AAACTCTCGA GACTTCTCTG TGAACTTCCC | 1978 |
| TACCCTACCC CCACAACACA AGCACCCCAG ACCTCACCTC CATCCCCCTC TGTCTG | 2034 |

(2) INFORMATION FOR SEQ ID NO:16:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..558

(xi) SEQUENCE DESCRIPTION: SEQ ID NO:16:

| | |
|---|---|
| CTG GAG CTG CGC CCG CGA TCT CGC TAC CGT TTA CAG CTG CGC GCC AGG<br>Leu Glu Leu Arg Pro Arg Ser Arg Tyr Arg Leu Gln Leu Arg Ala Arg<br>1                                5                        10                        15 | 48 |
| CTC AAC GGC CCC ACC TAC CAA GGT CCC TGG AGC TCG TGG TCG GAC CCA<br>Leu Asn Gly Pro Thr Tyr Gln Gly Pro Trp Ser Ser Trp Ser Asp Pro<br>                20                        25                        30 | 96 |
| ACT AGG GTG GAG ACC GCC ACC GAG ACC GCC TGG ATC TCC TTG GTG ACC<br>Thr Arg Val Glu Thr Ala Thr Glu Thr Ala Trp Ile Ser Leu Val Thr<br>                35                        40                        45 | 144 |
| GCT CTG CAT CTA GTG CTG GGC CTC AGC GCC GTC CTG GGC CTG CTG CTG<br>Ala Leu His Leu Val Leu Gly Leu Ser Ala Val Leu Gly Leu Leu Leu<br>50                                55                        60 | 192 |
| CTG AGG TGG CAG TTT CCT GCA CAC TAC AGG AGA CTG AGG CAT GCC CTG<br>Leu Arg Trp Gln Phe Pro Ala His Tyr Arg Arg Leu Arg His Ala Leu<br>65                                70                        75                      80 | 240 |
| TGG CCC TCA CTT CCA GAC CTG CAC CGG GTC CTA GGC CAG TAC CTT AGG<br>Trp Pro Ser Leu Pro Asp Leu His Arg Val Leu Gly Gln Tyr Leu Arg<br>                            85                        90                        95 | 288 |
| GAC ACT GCA GCC CTG AGC CCG CCC AAG GCC ACA GTC TCA GAT ACC TGT<br>Asp Thr Ala Ala Leu Ser Pro Pro Lys Ala Thr Val Ser Asp Thr Cys<br>                              100                        105                        110 | 336 |
| GAA GAA GTG GAA CCC AGC CTC CTT GAA ATC CTC CCC AAG TCC TCA GAG<br>Glu Glu Val Glu Pro Ser Leu Leu Glu Ile Leu Pro Lys Ser Ser Glu<br>            115                        120                        125 | 384 |
| AGG ACT CCT TTG CCC CTG TGT TCC TCC CAG GCC CAG ATG GAC TAC CGA<br>Arg Thr Pro Leu Pro Leu Cys Ser Ser Gln Ala Gln Met Asp Tyr Arg<br>130                                135                        140 | 432 |

```
AGA TTG CAG CCT TCT TGC CTG GGG ACC ATG CCC CTG TCT GTG TGC CCA        480
Arg Leu Gln Pro Ser Cys Leu Gly Thr Met Pro Leu Ser Val Cys Pro
145                 150                 155                 160

CCC ATG GCT GAG TCA GGG TCC TGC TGT ACC ACC CAC ATT GCC AAC CAT        528
Pro Met Ala Glu Ser Gly Ser Cys Cys Thr Thr His Ile Ala Asn His
                165                 170                 175

TCC TAC CTA CCA CTA AGC TAT TGG CAG CAG                                558
Ser Tyr Leu Pro Leu Ser Tyr Trp Gln Gln
            180                 185
```

(2) INFORMATION FOR SEQ ID NO:17:

(i) SEQUENCE CHARACTERISTICS:
        (A) LENGTH: 1307 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1146

(xi) SEQUENCE DESCRIPTION: SEQ ID NO:17:

```
ATC CTA CTG CTC AGC TAC GCA GCC AAC CGA CGG GGT CTC CCT TCG TGG         48
Ile Leu Leu Leu Ser Tyr Ala Ala Asn Arg Arg Gly Leu Pro Ser Trp
1               5                   10                  15

CTC CTG GGA CCC TGG TCC TTC CCT GTG ACT GTG GAT CTT CCA GGA GAT         96
Leu Leu Gly Pro Trp Ser Phe Pro Val Thr Val Asp Leu Pro Gly Asp
                20                  25                  30

GCA GTG ACA ATT GGA CTT CAG TGC TTT ACC TTG GAT CTG AAG ATG GTC        144
Ala Val Thr Ile Gly Leu Gln Cys Phe Thr Leu Asp Leu Lys Met Val
            35                  40                  45

ACC TGC CAG TGG CAG CAA CAA GAC CGC ACT AGC TCC CAA GGC TTC TTC        192
Thr Cys Gln Trp Gln Gln Gln Asp Arg Thr Ser Ser Gln Gly Phe Phe
        50                  55                  60

CGT CAC AGC AGG ACG AGG TGC TGC CCC ACA GAC AGG GAC CCC ACC TGG        240
Arg His Ser Arg Thr Arg Cys Cys Pro Thr Asp Arg Asp Pro Thr Trp
65                  70                  75                  80

GAG AAA TGT GAA GAG GAG GAA CCG CGT CCA GGA TCA CAG CCC GCT CTC        288
Glu Lys Cys Glu Glu Glu Glu Pro Arg Pro Gly Ser Gln Pro Ala Leu
                85                  90                  95

GTC TCC CGC TGC CAC TTC AAG TCA CGA AAT GAC AGT GTT ATT CAC ATC        336
Val Ser Arg Cys His Phe Lys Ser Arg Asn Asp Ser Val Ile His Ile
            100                 105                 110

CTT GTA GAG GTG ACC ACA GCG CAA GGT GCC GTT CAC AGC TAC CTG GGC        384
Leu Val Glu Val Thr Thr Ala Gln Gly Ala Val His Ser Tyr Leu Gly
        115                 120                 125

TCC CCT TTT TGG ATC CAC CAG GCT GTG CTC CTT CCC ACC CCG AGC CTG        432
Ser Pro Phe Trp Ile His Gln Ala Val Leu Leu Pro Thr Pro Ser Leu
130                 135                 140

CAC TGG AGG GAG GTC TCA AGT GGA AGG CTG GAG TTG GAG TGG CAG CAC        480
His Trp Arg Glu Val Ser Ser Gly Arg Leu Glu Leu Glu Trp Gln His
145                 150                 155                 160

CAG TCA TCT TGG GCA GCT CAA GAG ACC TGC TAC CAG CTC CGG TAC ACG        528
Gln Ser Ser Trp Ala Ala Gln Glu Thr Cys Tyr Gln Leu Arg Tyr Thr
                165                 170                 175

GGA GAA GGC CGT GAG GAC TGG AAG GTG CTG GAG CCA TCT CTC GGT GCC        576
Gly Glu Gly Arg Glu Asp Trp Lys Val Leu Glu Pro Ser Leu Gly Ala
            180                 185                 190

CGG GGA GGG ACC CTA GAG CTG CGC CCC CGA GCT CGC TAC AGC TTG CAG        624
Arg Gly Gly Thr Leu Glu Leu Arg Pro Arg Ala Arg Tyr Ser Leu Gln
```

```
                      195                 200                 205
CTG CGT GCC AGG CTC AAC GGC CCC ACC TAC CAA GGT CCC TGG AGC GCC      672
Leu Arg Ala Arg Leu Asn Gly Pro Thr Tyr Gln Gly Pro Trp Ser Ala
210                 215                 220

TGG TCT CCC CCA GCT AGG GTG TCC ACG GGC TCC GAG ACT GCT TGG ATC      720
Trp Ser Pro Pro Ala Arg Val Ser Thr Gly Ser Glu Thr Ala Trp Ile
225                 230                 235                 240

ACC TTG GTG ACT GCT CTG CTC CTG GTG CTG AGC CTC AGT GCC CTT CTG      768
Thr Leu Val Thr Ala Leu Leu Leu Val Leu Ser Leu Ser Ala Leu Leu
                245                 250                 255

GGC CTA CTG CTG CTA AAG TGG CAA TTT CCT GCG CAC TAC AGG AGA CTG      816
Gly Leu Leu Leu Leu Lys Trp Gln Phe Pro Ala His Tyr Arg Arg Leu
            260                 265                 270

AGG CAT GCT TTG TGG CCC TCG CTT CCA GAC CTA CAC CGG GTC CTA GGC      864
Arg His Ala Leu Trp Pro Ser Leu Pro Asp Leu His Arg Val Leu Gly
        275                 280                 285

CAG TAC CTC AGA GAC ACT GCA GCC CTA AGT CCT TCT AAG GCC ACG GTT      912
Gln Tyr Leu Arg Asp Thr Ala Ala Leu Ser Pro Ser Lys Ala Thr Val
    290                 295                 300

ACC GAT AGC TGT GAA GAA GTG GAA CCC AGC CTC CTG GAA ATC CTC CCT      960
Thr Asp Ser Cys Glu Glu Val Glu Pro Ser Leu Leu Glu Ile Leu Pro
305                 310                 315                 320

AAA TCC TCA GAG AGC ACT CCT TTA CCT CTG TGT CCC TCC CAA CCT CAG     1008
Lys Ser Ser Glu Ser Thr Pro Leu Pro Leu Cys Pro Ser Gln Pro Gln
                325                 330                 335

ATG GAC TAC AGA GGA CTG CAA CCT TGC CTG CGG ACC ATG CCC CTG TCT     1056
Met Asp Tyr Arg Gly Leu Gln Pro Cys Leu Arg Thr Met Pro Leu Ser
            340                 345                 350

GTG TGT CCA CCC ATG GCT GAG ACG GGG TCC TGC TGC ACC ACA CAC ATT     1104
Val Cys Pro Pro Met Ala Glu Thr Gly Ser Cys Cys Thr Thr His Ile
        355                 360                 365

GCC AAC CAC TCC TAC CTA CCA CTA AGC TAT TGG CAG CAG CCC              1146
Ala Asn His Ser Tyr Leu Pro Leu Ser Tyr Trp Gln Gln Pro
    370                 375                 380

TGAAGGCAGT CCCCATGCTA CTGCAGACCT ATACATTCCT ACACACTACC TTATCCATCC   1206

TCAACACCAT CCATTCTGTT GCCACCCCAC TCCCCCTCTG GCTTTATAAC ACTGATCACT   1266

CCAAGATGGC TGCTCACAAA TCCAGAGCTC TGTCTCTGCA G                      1307

(2) INFORMATION FOR SEQ ID NO:18:

(i) SEQUENCE CHARACTERISTICS:
        (A) LENGTH: 552 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..552

(xi) SEQUENCE DESCRIPTION: SEQ ID NO:18:

CTA GAG CTG CGC CCC CGA GCT CGC TAC AGC TTG CAG CTG CGT GCC AGG       48
Leu Glu Leu Arg Pro Arg Ala Arg Tyr Ser Leu Gln Leu Arg Ala Arg
1               5                   10                  15

CTC AAC GGC CCC ACC TAC CAA GGT CCC TGG AGC GCC TGG TCT CCC CCA       96
Leu Asn Gly Pro Thr Tyr Gln Gly Pro Trp Ser Ala Trp Ser Pro Pro
                20                  25                  30

GCT AGG GTG TCC ACG GGC TCC GAG ACT GCT TGG ATC ACC TTG GTG ACT      144
Ala Arg Val Ser Thr Gly Ser Glu Thr Ala Trp Ile Thr Leu Val Thr
            35                  40                  45
```

```
GCT CTG CTC CTG GTG CTG AGC CTC AGT GCC CTT CTG GGC CTA CTG CTG           192
Ala Leu Leu Leu Val Leu Ser Leu Ser Ala Leu Leu Gly Leu Leu Leu
 50                  55                  60

CTA AAG TGG CAA TTT CCT GCG CAC TAC AGG AGA CTG AGG CAT GCT TTG           240
Leu Lys Trp Gln Phe Pro Ala His Tyr Arg Arg Leu Arg His Ala Leu
 65                  70                  75                  80

TGG CCC TCG CTT CCA GAC CTA CAC CGG GTC CTA GGC CAG TAC CTC AGA           288
Trp Pro Ser Leu Pro Asp Leu His Arg Val Leu Gly Gln Tyr Leu Arg
                 85                  90                  95

GAC ACT GCA GCC CTA AGT CCT TCT AAG GCC ACG GTT ACC GAT AGC TGT           336
Asp Thr Ala Ala Leu Ser Pro Ser Lys Ala Thr Val Thr Asp Ser Cys
            100                 105                 110

GAA GAA GTG GAA CCC AGC CTC CTG GAA ATC CTC CCT AAA TCC TCA GAG           384
Glu Glu Val Glu Pro Ser Leu Leu Glu Ile Leu Pro Lys Ser Ser Glu
            115                 120                 125

AGC ACT CCT TTA CCT CTG TGT CCC TCC CAA CCT CAG ATG GAC TAC AGA           432
Ser Thr Pro Leu Pro Leu Cys Pro Ser Gln Pro Gln Met Asp Tyr Arg
        130                 135                 140

GGA CTG CAA CCT TGC CTG CGG ACC ATG CCC CTG TCT GTG TGT CCA CCC           480
Gly Leu Gln Pro Cys Leu Arg Thr Met Pro Leu Ser Val Cys Pro Pro
145                 150                 155                 160

ATG GCT GAG ACG GGG TCC TGC TGC ACC ACA CAC ATT GCC AAC CAC TCC           528
Met Ala Glu Thr Gly Ser Cys Cys Thr Thr His Ile Ala Asn His Ser
                165                 170                 175

TAC CTA CCA CTA AGC TAT TGG CAG                                           552
Tyr Leu Pro Leu Ser Tyr Trp Gln
            180
```

(2) INFORMATION FOR SEQ ID NO:19:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..111

(xi) SEQUENCE DESCRIPTION: SEQ ID NO:19:

```
TGG CAA TTT CCT GCG CAC TAC AGG AGA CTG AGG CAT GCT TTG TGG CCC            48
Trp Gln Phe Pro Ala His Tyr Arg Arg Leu Arg His Ala Leu Trp Pro
 1                   5                  10                  15

TCG CTT CCA GAC CTA CAC CGG GTC CTA GGC CAG TAC CTC AGA GAC ACT            96
Ser Leu Pro Asp Leu His Arg Val Leu Gly Gln Tyr Leu Arg Asp Thr
                20                  25                  30

GCA GCC CTA AGT CCT                                                       111
Ala Ala Leu Ser Pro
             35
```

(2) INFORMATION FOR SEQ ID NO:20:

(i) SEQUENCE CHARACTERISTICS:
        (A) LENGTH: 1216 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..852

(xi) SEQUENCE DESCRIPTION: SEQ ID NO:20:

| | | | | | | | | | | | | | | | | |
|---|---|---|---|---|---|---|---|---|---|---|---|---|---|---|---|---|
| ATG | GCG | TGT | TCA | ACG | CTC | CCA | AAA | TCC | CCT | AAA | GAT | AAG | ATT | GAC | CCG | 48 |
| Met | Ala | Cys | Ser | Thr | Leu | Pro | Lys | Ser | Pro | Lys | Asp | Lys | Ile | Asp | Pro | |
| 1 | | | | 5 | | | | | 10 | | | | | 15 | | |
| CGG | GAC | CTC | CTA | ATC | CCC | TTA | ATT | CTC | TTC | CTG | TCT | CTC | AAA | GGG | GCC | 96 |
| Arg | Asp | Leu | Leu | Ile | Pro | Leu | Ile | Leu | Phe | Leu | Ser | Leu | Lys | Gly | Ala | |
| | | | 20 | | | | | 25 | | | | | 30 | | | |
| AGA | TCC | GCA | GCA | CCC | GGC | TCC | AGC | CCT | CAC | CAG | GTC | TAC | AAC | ATT | ACC | 144 |
| Arg | Ser | Ala | Ala | Pro | Gly | Ser | Ser | Pro | His | Gln | Val | Tyr | Asn | Ile | Thr | |
| | | 35 | | | | | 40 | | | | | 45 | | | | |
| TGG | GAA | GTG | ACC | AAT | GGG | GAT | CGG | GAG | ACA | GTA | TGG | GCA | ATA | TCA | GGA | 192 |
| Trp | Glu | Val | Thr | Asn | Gly | Asp | Arg | Glu | Thr | Val | Trp | Ala | Ile | Ser | Gly | |
| | 50 | | | | | 55 | | | | | 60 | | | | | |
| CGT | CTT | TAT | GTC | TCT | GGG | CGG | GAC | CCG | GGG | CTT | ACT | TTC | GGG | ATC | CGA | 240 |
| Arg | Leu | Tyr | Val | Ser | Gly | Arg | Asp | Pro | Gly | Leu | Thr | Phe | Gly | Ile | Arg | |
| 65 | | | | | 70 | | | | | 75 | | | | | 80 | |
| CTC | AGA | TAT | CAA | AAT | CTA | GGA | CCT | CGG | GTC | CCG | ATA | GGA | CCG | AAC | CCC | 288 |
| Leu | Arg | Tyr | Gln | Asn | Leu | Gly | Pro | Arg | Val | Pro | Ile | Gly | Pro | Asn | Pro | |
| | | | | 85 | | | | | 90 | | | | | 95 | | |
| GTC | CTG | GCA | GAC | CTA | GAG | CTG | CGC | CCC | CGA | GCT | CGC | TAC | AGC | TTG | CAG | 336 |
| Val | Leu | Ala | Asp | Leu | Glu | Leu | Arg | Pro | Arg | Ala | Arg | Tyr | Ser | Leu | Gln | |
| | | | 100 | | | | | 105 | | | | | 110 | | | |
| CTG | CGT | GCC | AGG | CTC | AAC | GGC | CCC | ACC | TAC | CAA | GGT | CCC | TGG | AGC | GCC | 384 |
| Leu | Arg | Ala | Arg | Leu | Asn | Gly | Pro | Thr | Tyr | Gln | Gly | Pro | Trp | Ser | Ala | |
| | | 115 | | | | | 120 | | | | | 125 | | | | |
| TGG | TCT | CCC | CCA | GCT | AGG | GTG | TCC | ACG | GGC | TCC | GAG | ACT | GCT | TGG | ATC | 432 |
| Trp | Ser | Pro | Pro | Ala | Arg | Val | Ser | Thr | Gly | Ser | Glu | Thr | Ala | Trp | Ile | |
| | 130 | | | | | 135 | | | | | 140 | | | | | |
| ACC | TTG | GTG | ACT | GCT | CTG | CTC | CTG | GTG | CTG | AGC | CTC | AGT | GCC | CTT | CTG | 480 |
| Thr | Leu | Val | Thr | Ala | Leu | Leu | Leu | Val | Leu | Ser | Leu | Ser | Ala | Leu | Leu | |
| 145 | | | | | 150 | | | | | 155 | | | | | 160 | |
| GGC | CTA | CTG | CTG | CTA | AAG | TGG | CAA | TTT | CCT | GCG | CAC | TAC | AGG | AGA | CTG | 528 |
| Gly | Leu | Leu | Leu | Leu | Lys | Trp | Gln | Phe | Pro | Ala | His | Tyr | Arg | Arg | Leu | |
| | | | | 165 | | | | | 170 | | | | | 175 | | |
| AGG | CAT | GCT | TTG | TGG | CCC | TCG | CTT | CCA | GAC | CTA | CAC | CGG | GTC | CTA | GGC | 576 |
| Arg | His | Ala | Leu | Trp | Pro | Ser | Leu | Pro | Asp | Leu | His | Arg | Val | Leu | Gly | |
| | | | 180 | | | | | 185 | | | | | 190 | | | |
| CAG | TAC | CTC | AGA | GAC | ACT | GCA | GCC | CTA | AGT | CCT | TCT | AAG | GCC | ACG | GTT | 624 |
| Gln | Tyr | Leu | Arg | Asp | Thr | Ala | Ala | Leu | Ser | Pro | Ser | Lys | Ala | Thr | Val | |
| | | 195 | | | | | 200 | | | | | 205 | | | | |
| ACC | GAT | AGC | TGT | GAA | GAA | GTG | GAA | CCC | AGC | CTC | CTG | GAA | ATC | CTC | CCT | 672 |
| Thr | Asp | Ser | Cys | Glu | Glu | Val | Glu | Pro | Ser | Leu | Leu | Glu | Ile | Leu | Pro | |
| | 210 | | | | | 215 | | | | | 220 | | | | | |
| AAG | TCC | TCA | GAG | AGC | ACT | CCT | TTA | CCT | CTG | TGT | CCC | TCC | CAA | CCT | CAG | 720 |
| Lys | Ser | Ser | Glu | Ser | Thr | Pro | Leu | Pro | Leu | Cys | Pro | Ser | Gln | Pro | Gln | |
| 225 | | | | | 230 | | | | | 235 | | | | | 240 | |
| ATG | GAC | TAC | AGA | GGA | CTG | CAA | CCT | TGC | CTG | CGG | ACC | ATG | CCC | CTG | TCT | 768 |
| Met | Asp | Tyr | Arg | Gly | Leu | Gln | Pro | Cys | Leu | Arg | Thr | Met | Pro | Leu | Ser | |
| | | | | 245 | | | | | 250 | | | | | 255 | | |
| GTG | TGT | CCA | CCC | ATG | GCT | GAG | ACG | GGG | TCC | TGC | TGC | ACC | ACA | CAC | ATT | 816 |
| Val | Cys | Pro | Pro | Met | Ala | Glu | Thr | Gly | Ser | Cys | Cys | Thr | Thr | His | Ile | |
| | | | 260 | | | | | 265 | | | | | 270 | | | |
| GCC | AAC | CAC | TCC | TAC | CTA | CCA | CTA | AGC | TAT | TGG | CAG | TAGTCCTGAA | | | | 862 |
| Ala | Asn | His | Ser | Tyr | Leu | Pro | Leu | Ser | Tyr | Trp | Gln | | | | | |
| | | 275 | | | | | 280 | | | | | | | | | |

GGCAGTCCCC ATGCTACTGC AGACCTATAC ATTCCTACAC ACTACCTTAT CCATCGACCT    922

CTAGGCCTAG TAAGAGATAG TATGGCCAAA TTAAGAGAGA GACTCACTCA GAGACAAAAA    982

CTATTTGAGT CGAGCCAAGG ATGGTTCGAA GGATTGTTTA ACAGATCCCC CTGGTTTACC    1042

```
ACGTTAATAT CCACCATCAT GGGGCCTCTC ATTATACTCC TACTAATTCT GCTTTTTGGA      1102

CCCTGCATTC TTAATCGATT AGTTCAATTT GTTAAAGACA GGATCTCAGT AGTCCAGGCT      1162

TTAGTCCTGA CTCAACAATA CCACCAGCTA AAACCACTAG AATACGAGCC ATGA            1216
```

(2) INFORMATION FOR SEQ ID NO:21:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:21:

```
Trp Ser Xaa Trp Ser
1               5
```

(2) INFORMATION FOR SEQ ID NO:22:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:22:

```
Trp Ser Ala Trp Ser
1               5
```

(2) INFORMATION FOR SEQ ID NO:23:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:23:

```
Trp Ser Ser Trp Ser
1               5
```

(2) INFORMATION FOR SEQ ID NO:24:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO:24:

```
Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
                20                  25                  30

Arg Ser Ala Ala Pro Gly Ser Ser Pro His Gln Val Tyr Asn Ile Thr
            35                  40                  45

Trp Glu Val Thr Asn Gly Asp Arg Glu Thr Val Trp Ala Ile Ser Gly
        50                  55                  60

Arg Leu Tyr Val Ser Gly Arg Asp Pro Gly Leu Thr Phe Gly Ile Arg
65                  70                  75                  80

Leu Arg Tyr Gln Asn Leu Gly Pro Arg Val Pro Ile Gly Pro Asn Pro
```

```
                    85                  90                  95
Val Leu Ala Asp Leu Glu Leu Arg Pro Arg Ala Arg Tyr Ser Leu Gln
                100                 105                 110

Leu Arg Ala Arg Leu Asn Gly Pro Thr Tyr Gln Gly Pro Trp Ser Ala
            115                 120                 125

Trp Ser Pro Pro Ala Arg Val Ser Thr Gly Ser Glu Thr Ala Trp Ile
        130                 135                 140

Thr Leu Val Thr Ala Leu Leu Val Leu Ser Leu Ser Ala Leu Leu
145                 150                 155                 160

Gly Leu Leu Leu Leu Lys Trp Gln Phe Pro Ala His Tyr Arg Arg Leu
                165                 170                 175

Arg His Ala Leu Trp Pro Ser Leu Pro Asp Leu His Arg Val Leu Gly
                180                 185                 190

Gln Tyr Leu Arg Asp Thr Ala Ala Leu Ser Pro Ser Lys Ala Thr Val
                195                 200                 205

Thr Asp Ser Cys Glu Glu Val Glu Pro Ser Leu Leu Glu Ile Leu Pro
        210                 215                 220

Lys Ser Ser Glu Ser Thr Pro Leu Pro Leu Cys Pro Ser Gln Pro Gln
225                 230                 235                 240

Met Asp Tyr Arg Gly Leu Gln Pro Cys Leu Arg Thr Met Pro Leu Ser
                245                 250                 255

Val Cys Pro Pro Met Ala Glu Thr Gly Ser Cys Cys Thr Thr His Ile
                260                 265                 270

Ala Asn His Ser Tyr Leu Pro Leu Ser Tyr Trp Gln
                275                 280

(2) INFORMATION FOR SEQ ID NO:25:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (vii) IMMEDIATE SOURCE:
        (B) CLONE: Extracellular domain of v-mpl (xi) SEQUENCE DESCRIPTION: SEQ ID NO:25:

Glu Leu Arg Pro Arg Ala Arg Tyr Ser Leu Gln Leu Arg Ala Arg Leu
1               5                   10                  15

Asn Gly Pro Thr Tyr Gln Gly Pro Trp Ser Ala Trp Ser Pro Pro Ala
                20                  25                  30

(2) INFORMATION FOR SEQ ID NO:26:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (vii) IMMEDIATE SOURCE:
        (B) CLONE: mIL-3RI (xi) SEQUENCE DESCRIPTION: SEQ ID NO:26:

Lys Leu Phe Leu Pro Asn Ser Ile Tyr Ala Ala Arg Val Arg Thr Arg
1               5                   10                  15

Leu Ser Ala Gly Ser Leu Ser Gly Arg Pro Ser Arg Trp Ser Pro Glu
                20                  25                  30
```

Val (2) INFORMATION FOR SEQ ID NO:27:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (vii) IMMEDIATE SOURCE:
        (B) CLONE: mIL-3RII (xi) SEQUENCE DESCRIPTION: SEQ ID NO:27:

```
Gln Leu Glu Pro Asp Thr Ser Tyr Cys Ala Arg Val Arg Val Lys Pro
 1               5                  10                  15
Ile Ser Asp Tyr Asp Gly Ile Trp Ser Glu Trp Ser Asn Glu Tyr
            20                  25                  30
```

(2) INFORMATION FOR SEQ ID NO:28:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (vii) IMMEDIATE SOURCE:
        (B) CLONE: Murine receptor for EPO (mEPO R)

(xi) SEQUENCE DESCRIPTION: SEQ ID NO:28:

```
Asn Leu Arg Gly Gly Thr Arg Tyr Thr Phe Ala Val Arg Ala Arg Met
 1               5                  10                  15
Ala Glu Pro Ser Phe Ser Gly Phe Trp Ser Ala Trp Ser Glu Pro
            20                  25                  30
```

(2) INFORMATION FOR SEQ ID NO:29:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (vii) IMMEDIATE SOURCE:
        (B) CLONE: Murine receptor for IL-4 (mIL4R)

(xi) SEQUENCE DESCRIPTION: SEQ ID NO:29:

```
Ile Leu Met Ser Gly Val Tyr Tyr Thr Ala Arg Val Arg Val Arg Ser
 1               5                  10                  15
Gln Ile Leu Thr Gly Thr Trp Ser Glu Trp Ser Pro Ser Ile
            20                  25                  30
```

(2) INFORMATION FOR SEQ ID NO:30:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (vii) IMMEDIATE SOURCE:
        (B) CLONE: Beta chain of receptor for IL-2 (hIL2R)

(xi) SEQUENCE DESCRIPTION: SEQ ID NO:30:

```
Thr Leu Thr Pro Asp Thr Gln Tyr Glu Phe Gln Val Arg Val Lys Pro
1               5                   10                  15

Leu Gln Gly Glu Phe Thr Thr Trp Ser Pro Trp Ser Gln Pro Leu
            20                  25                  30

(2) INFORMATION FOR SEQ ID NO:31:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (vii) IMMEDIATE SOURCE:
        (B) CLONE: Human receptor for IL-6 (hIL6R)

(xi) SEQUENCE DESCRIPTION: SEQ ID NO:31:

Ile His Asp Ala Trp Ser Gly Leu Arg His Val Val Gln Leu Arg Ala
1               5                   10                  15

Gln Glu Glu Phe Cys Gly Glu Trp Ser Glu Trp Ser Pro Glu Ala
            20                  25                  30

(2) INFORMATION FOR SEQ ID NO:32:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (vii) IMMEDIATE SOURCE:
        (B) CLONE: Human receptor for IL-7 (hIL7R)

(xi) SEQUENCE DESCRIPTION: SEQ ID NO:32:

Lys Leu Gln Pro Ala Ala Met Tyr Glu Ile Lys Val Arg Ser Ile Pro
1               5                   10                  15

Asp His Tyr Phe Lys Gly Phe Trp Ser Glu Trp Ser Pro Ser Tyr
            20                  25                  30

(2) INFORMATION FOR SEQ ID NO:33:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (vii) IMMEDIATE SOURCE:
        (B) CLONE: Murine receptor for IL-7 (mIL7R)

(xi) SEQUENCE DESCRIPTION: SEQ ID NO:33:

Lys Leu Arg Pro Lys Ala Met Tyr Glu Ile Lys Val Arg Ser Ile Pro
1               5                   10                  15

His His Asp Tyr Phe Lys Gly Phe Trp Ser Glu Trp Ser Pro Ser Ser
            20                  25                  30

(2) INFORMATION FOR SEQ ID NO:34:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:34:
```

-continued

```
Leu Pro Tyr Xaa Val Arg Val Xaa Phe Gly Trp Ser Glu Trp Ser Pro
1               5                   10                  15
Glu
```

NUCLEIC ACID ENCODING POLYPEPTIDE OF A GROWTH FACTOR RECEPTOR FAMILY

CROSS REFERENCE TO RELATED APPLICATION

The present application is a national stage application of PCT/FR90/00762, filed Oct. 19, 1990.

BACKGROUND OF THE INVENTION

Myeloproliferative diseases are diseases in which hematopoietic stem cells exhibit an impairment in their differentiation capacity and/or an impairment of their dependence on a specific growth factor.

Blood cells derive from a small number of stem cells capable of self-nenewal which generate progenitor cells irreversibly committed to the production of one or a few hematopoietic lines. Precise control of each step of differentiation is necessary in order to ensure a stable level of the different specialized cells as well as to provide a precise response to stimulations caused by stress. The controls are usually due to the effect of interactions between cells, either resulting from contact with the hematopoietic microenvironment or from the release of specific cytokines. The breakdown of the control systems leads either to cytopenias or to an uncontrolled cellular proliferation which may affect one or more lines depending on the nature of the lesion. The proliferation of several hematopoietic lines may lead to a myeloproliferative disease. Such diseases can be induced by retroviruses carrying oncogenes such as the retrovirus MPLV, an abbreviation for "myeloproliferative leukemia virus" which is a retrovirus defective with respect to its replication.

It is known that the murine retrovirus MPLV causes a severe hematological disorder in adult mice of most strains, characterized by a dramatic proliferation and a differentiation of several hematopoietic lines. The most acute aspect of this disease is the suppression of the in vitro dependence on growth factors for most of the hematopoietic progenitor cells. The natural MPLV isolate has been described as being a complex of two viral entities: a murine virus F-MuLV (Friend replication competent ecotropic murine leukemia virus) and a virus defective with respect to its replication now designated by the term MPLV. The pseudotyping of the defective particles with other ecotropic or amphotropic MuLV viruses enables the initial disease to be reproduced. It has been shown that the proviral DNA of MPLV and the DNA of F-MuLV are structurally similar except in the envelope region.

The inventors have now identified a sequence of cellular origin transduced in the rearranged gene of the MPLV envelope and which proves to be conserved in the mammalian genome.

The identification of this sequence has enabled its importance in phenomena which have similarities with a myeloproliferative disease to be demonstrated.

The invention thus relates to a polypeptide capable of playing a role when it is produced by a virus of the MPLV type in the disturbances caused during myeloproliferative diseases. The invention also relates to nucleotide sequences coding for this polypeptide.

The inventors have made the very interesting observation that the protein sequence of the polypeptide of the invention exhibits pronounced analogies with certain amino acid sequences of growth factor receptors. Consequently, the invention makes possible the identification of the mechanisms of the disease linked to the infection by the retrovirus MPLV and suggests agents for the detection of a disease of the same type in man and optionally, for its treatment.

(B) Demonstration of the specificity of the probes derived from the MPLV envelope by northern analysis. Poly $A^+$ RNA was obtained from NIH 3T3 cells infected with the amphotropic 4070 pseudotype of MPLV (5 µg, lanes A) or with the clone F-MuLV 57 (1 µg, lanes B), and the nonproducing Mus dunni clone 2 infected with MPLV (15 µg, lanes C). The Northern blot was then hybridized with the probe E57BS derived from the envelope of F-MuLV, labeled according to the nick-translation procedure (FIG. 1B), or with the two RNA probes derived from the envelope of MPLV, SacI-PstI (FIG. 1C) and PstI-PstI (FIG. 1D). The lambda/HindIII DNA molecular weight marker is present in lane M of all three FIGS. 1B–D. The black arrows and the open arrows indicate the positions of the genomic and subgenomic RNA of the envelope of F-MuLV and MPLV, respectively.

Figure 2A:
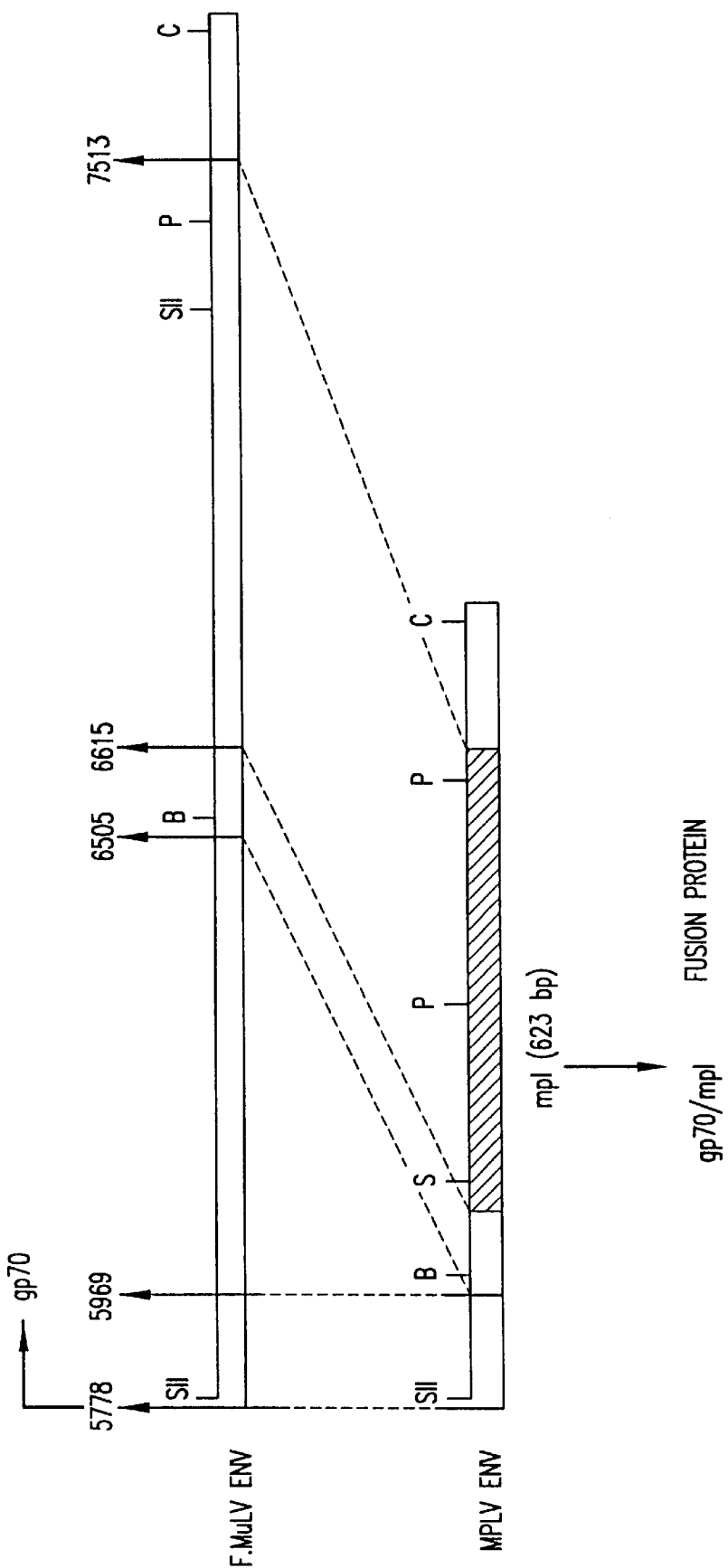

FIGS. 2A and B: (A) Schematic representation of the rearranged env region of MPLV (SEQ ID NO:24). The hatched box represents mpl, the open boxes represent the env sequence s of F-MuLV. The asterisk in the mpl domain indicates the stop codon.

(B) The amino acid sequence deduced for the env region of MPLV (SEQ ID NO:24). In the 284 amino acid reading frame, amino acids 1 to 100 correspond to the sequences derived from the env gene of F-MuLV. The 184 amino acids specific for mpl are indicated in the boxes. The arrow heads indicate the junction with the specific mpl sequence, respectively. The asterisks indicate the potential N-glycosylation sites (Asn-X-Ser/Thr). The underlined sequences represent the signal peptide of gp70, and the hydrophobic transmembrane domain is written in bold letters.

Figure 3:
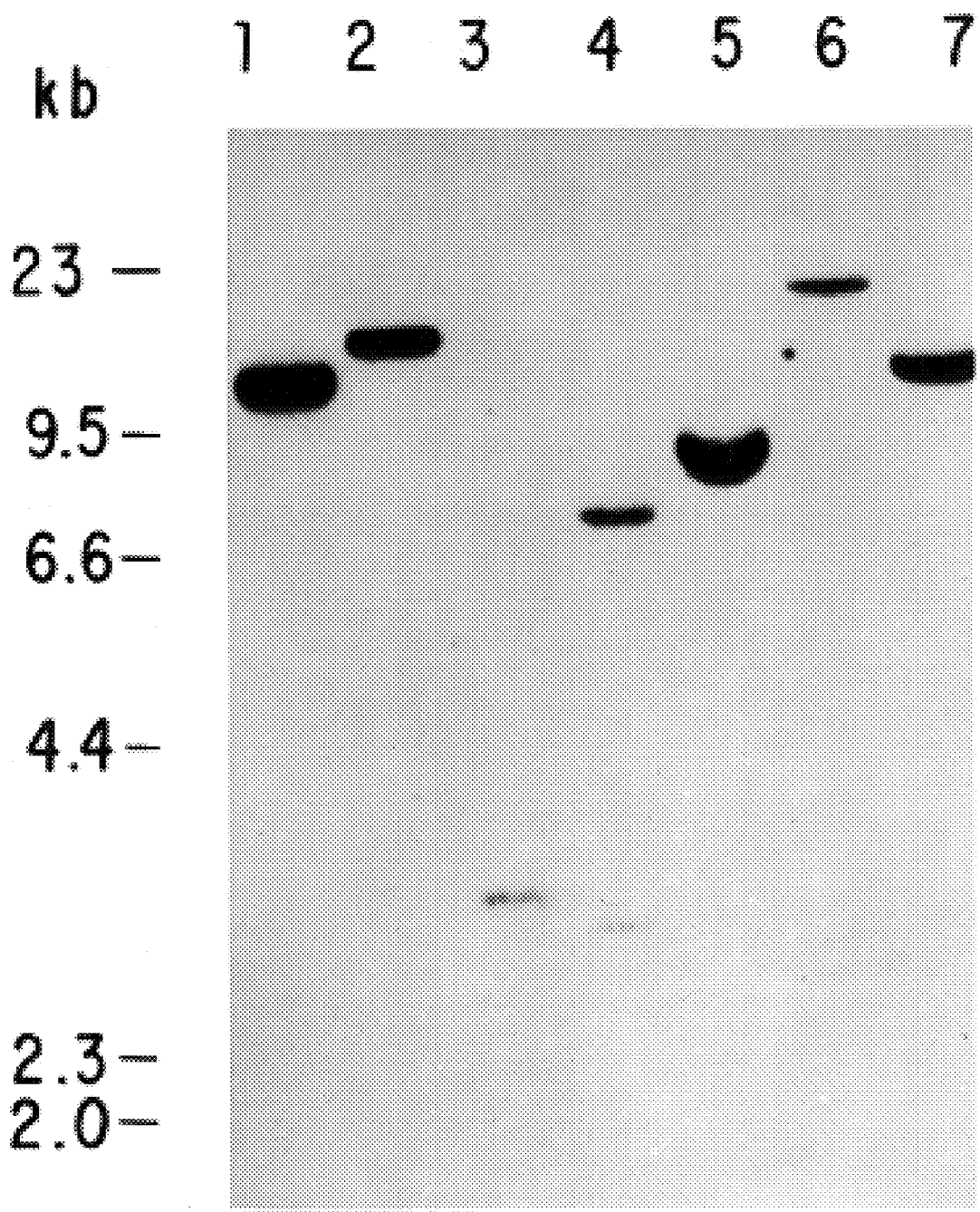

FIG. 3: Southern analysis of DNA from a variety of species, or Zoo blot, is provided. The blot was prepared with 10 µg of high molecular weight DNA, digested with EcoRI, from ICFW mice (lane 1), Mus spretus (lane 2), rat (lane 3), mink (lane 4), cow (lane 5), dog (lane 6), and human (lane 7), and was hybridized with the RNA probes SacI-PestI and PstI-PstI under stringent conditions and washed according to the procedure described in the "Experimental procedures".

Figure 4:
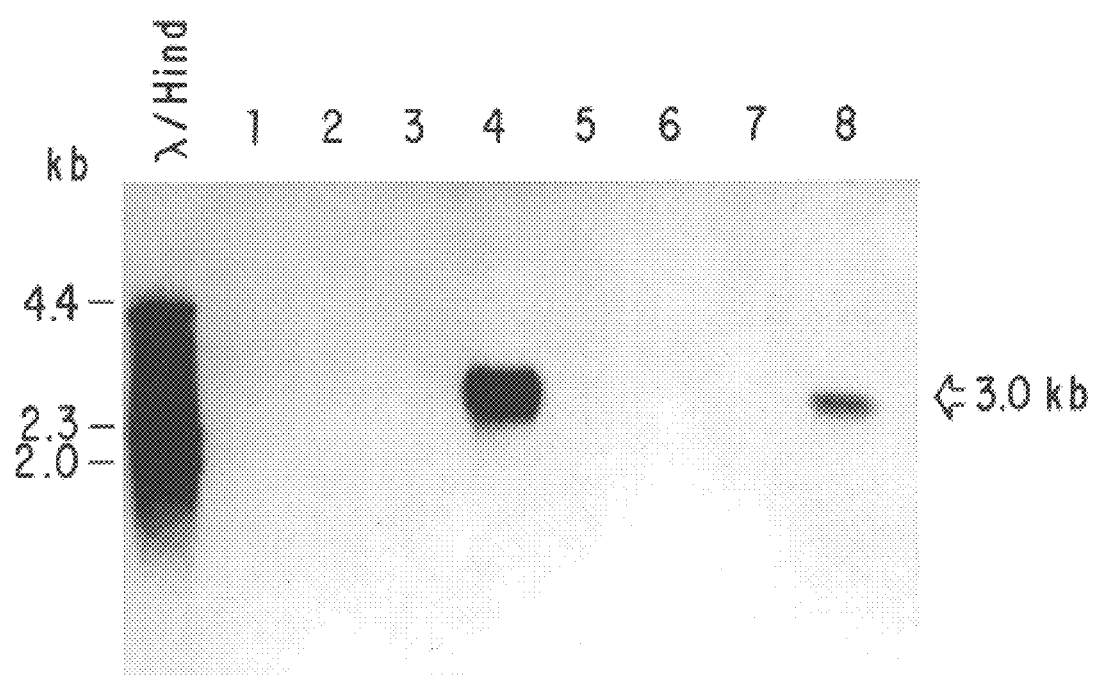

FIG. 4: Expression of c-mpl in different organs of the mouse. A Northern blot prepared from RNA poly $A^+$ (5 µg) of mouse brain (lane 1), liver (lane 2), salivary gland (lane 3), spleen (lane 4), kidney (lane 5), testicles (lane 6), thymus (lane 7), and fetal liver (lane 8) was hybridized with the RNA probes SacI-PstI and PstI-PstI. The conditions of hybridization and washing are described in the "Experimental procedures".

Figure 5:
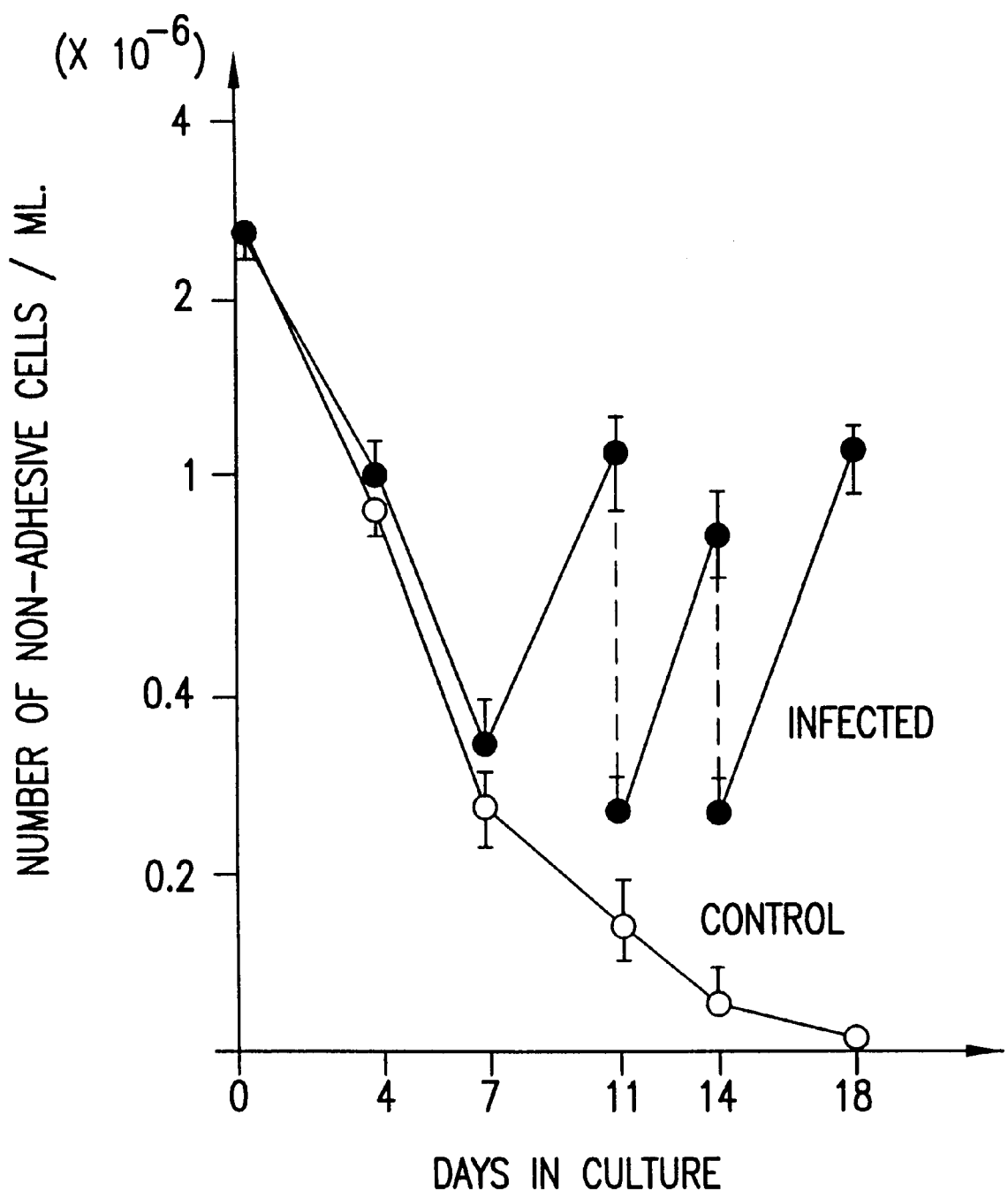

FIG. 5: Establishment of in vitro cells lines infected by MPLV. The bone marrow cells of normal C57BL/6 mice were infected in vitro with MPLV uncontaminated with auxiliary virus. The circles represent the mean values±standard deviation of the non-adhesive cells for five infected cultures (black circles) or five control cultures (white circles). The transfers of non-adhesive cell populations are shown by dashes.

Figure 6:
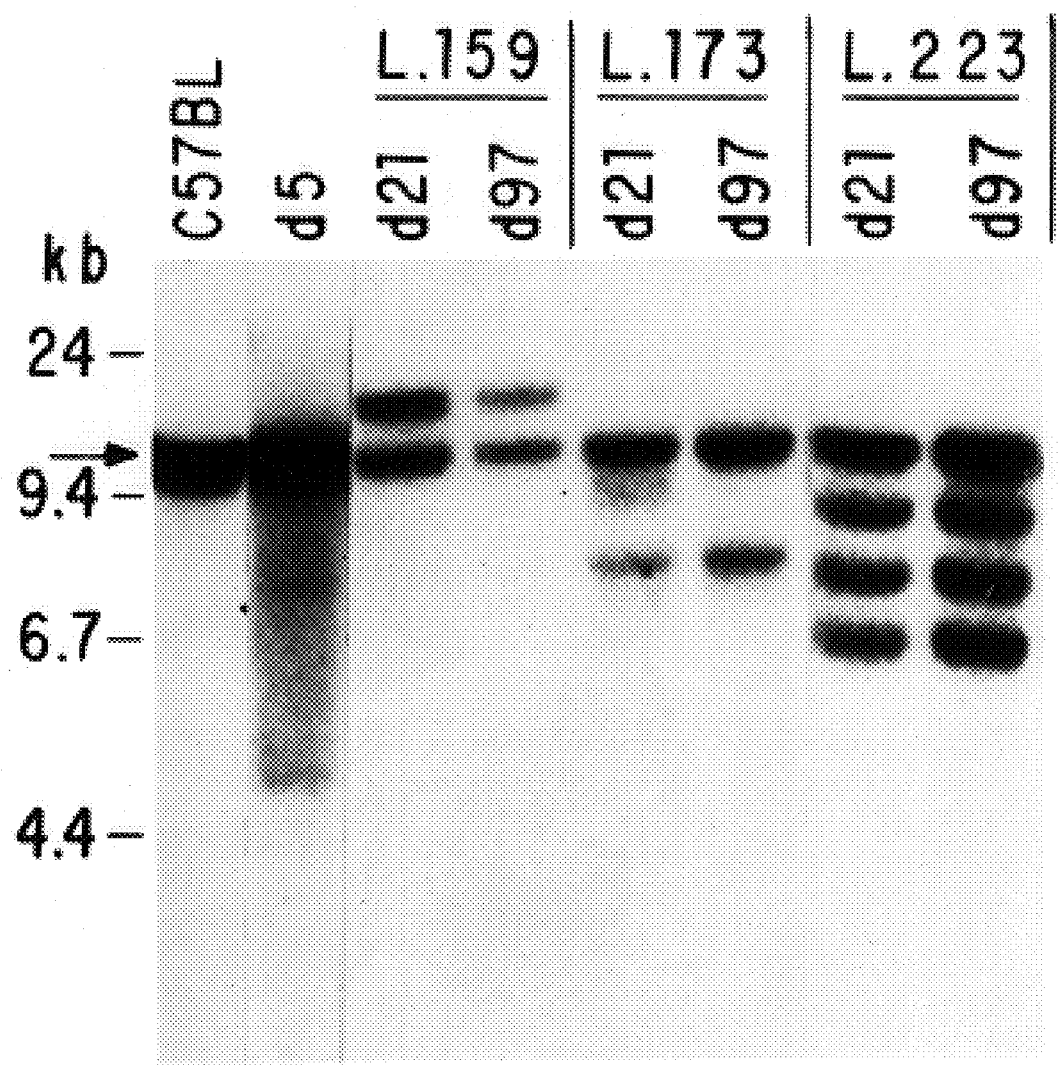

FIG. 6: Southern blot analysis of the proviral integration sites in the cultures infected with MPLV. The DNAs were obtained from the cell lines L159, L173 and L223, at 5, 21, and 97 days after the infection and were digested with EcoRI. Southern blots were prepared from the DNAs and hybridized with the SacI-PstI and PstI-PstI RNA probes of v-mpl. On day 97, L159 contained myeloblasts, L173 mastocytes, L223 megacaryocytes and erythbroblasts. The arrow indicates c-mpl.

FIG. 7: Comparison of the amino acid sequences of the extracellular domain of v-mpl (SEQ ID NO:25) with that of the receptors for the hematopoietic cytokines. The extracellular domains of the receptor for murine IL-3 (SEQ ID NOS:26 and 27), the murine receptor for EPO (SEQ ID NO:28), the murine receptor for IL-4 (SEQ ID NO:29), the beta chain of the receptor for IL-2 (SEQ ID NO:30), the human receptor for IL-6 (SEQ ID NO:31), and the human and murine receptors for IL-7 (SEQ ID NOS:32 and 33, respectively) were aligned with v-mpl. The conserved amino acid residues are placed in boxes. The consensus sequence (SEQ ID NO:34) is that which was described by Itoh et al. 1990 (Science, Vol. 247, p. 324–327).

SUMMARY OF THE INVENTION

The invention thus relates to a polypeptide characterized in that it corresponds to the amino acid sequence designated by SEQ ID NO:1 in the list of sequences, i.e., in that it comprises the sequence SEQ ID NO:1 or a fragment of this sequence provided that the polypeptide meets at least one of the following conditions:

a) when it is produced from the genome of the retrovirus MPLV, it is capable of causing and/or promoting in vitro and in vivo the proliferation of the hematopoietic cell lines, b) it is implicated in vitro or in vivo in the cellular differentiation of hematopoietic cell lines when it is produced from the genome of the MPLV retrovirus, c) it is capable of intervening in vivo in a function of a receptor for a hematopoietic growth factor, either at the level of the binding of a ligand, or at the level of signal transmission, d) it is recognized by antibodies directed against the amino acid sequence shown in the sequence SEQ ID NO:1, or also in that it is an amino acid sequence exhibiting a homology of at least 80%, and preferably 88%, with the fragment represented by SEQ ID NO:2, contained in the amino acid sequence (SEQ ID NO:1.

The capacity of a given polypeptide to behave as a growth factor receptor can be characterized by implementing one of the following tests.

The invention makes it possible to detect the potential capacity of a polypeptide of the invention to behave like a receptor and to bind a ligand. It is equally possible to investigate whether the expression of the test polypeptide by the MPLV virus previously modified by the nucleotide sequence coding for this polypeptide, integrated at the site usually containing the nucleotide sequence v-mpl, leads to the in vitro proliferation of cells transformed with MPLV containing the test polypeptide.

The conditions for carrying out this test are those used for the experiments reported hereafter, which correspond to the immortalization of bone marrow cells in culture by MPLV.

DETAILED DESCRIPTION OF THE PREFERRED EMBODIMENTS OF THE INVENTION

In order to detect whether a nucleotide sequence which codes for a polypeptide of the invention is capable of being implicated in signal transmission, it is possible to modify MPLV at the site which usually contains the sequence v-mpl by a nucleotide sequence of the invention from which a selected nucleotide fragment, whose possible role in signal transmission it is desired to determine, has previously be removed. MPLV thus modified may be infected, for example, with bone marrow cells in accordance with what is described in the examples. It is then observed whether the elimination of the nucleotide fragment, referred to above leads to the absence of cellular proliferation.

Another test to detect whether a polypeptide of the invention behaves as a receptor capable of both binding a selected molecule and of transmitting a signal after binding this molecule is the following:

Cells not naturally expressing the test polypeptide are transformed with the latter. The cells thus transformed are placed in the presence of a selected molecule capable of behaving as a ligand and their capacity to respond to this molecule is determined; in particular, by observing whether there is cellular proliferation or not.

Particularly useful peptides complying with the definition of the invention previously given are, for example, polypeptides comprising an amino acid sequence WSXWS (SEQ ID NO:21), in which X is any amino acid and preferably X corresponds to arginine or serine.

The sequence WSAWS (SEQ ID NO:22) corresponds to the fragment comprised in v-mpl or in the equivalent sequence in the mouse, and the sequence WSSWS (SEQ ID NO:23) corresponds to the h-mpl fragment of the human cellular.

In a very interesting manner it has been noted that the peptide WSXWS (SEQ ID NO:24) may be implicated in the in vivo differentiation effect of hematopoietic lines, observed when they are infected by a MPLV retrovirus.

The invention also relates to all of the polypeptides satisfying the preceding conditions and capable of inducing or taking part in the in vitro cellular differentiation of hematopoietic lines.

Other preferred polypeptides according to the invention are peptides characterized in that they are composed of an amino acid sequence corresponding to the sequence identified in the list of the sequences under the reference SEQ ID NO:3

Preferred polypeptides complying with the general definition above are the polypeptides corresponding to one of the sequences identified under the following references SEQ ID NO:2, SEQ ID NO:4, SEQ ID NO:5, SEQ ID NO:6, SEQ ID NO:7, SEQ ID NO:8, SEQ ID NO:9, SEQ ID NO: 10, SEQ ID NO:11.

Another polypeptide according to the invention is characterized in that it is encoded in a nucleotide sequence capable of hybridizing under stringent conditions with the specific probes for MPLV corresponding to the fragments sacl-pstI and pstI-pscI of 300 base pairs each shown in FIG. 1.

The probes may be DNA probes or RNA probes.

Also included in the framework of the invention is a polypeptide encoded in a nucleotide sequence capable of hybridizing with one of the preceding probes.

The invention also relates to a polypeptide included in the preceding definitions, characterized in that it corresponds to one of the amino acid sequences identified in the list of sequences by the following references SEQ ID NO:12, SEQ ID NO:13.

The invention relates in addition to a growth factor receptor, characterized in that it is composed of the amino acid sequence identified as SEQ ID NO:1.

The invention also relates to a soluble form of the receptor consisting in particular of the extracellular domain represented by the polypeptide sequence designated by SEQ ID NO:7 in man or SEQ ID NO:10 in the mouse.

Also forming part of the invention are fusion proteins, characterized in that they are composed of a polypeptide of the invention in combination with a defined amino acid sequence, in particular with the gp70 of MPLV, in particular in that it is the amino acid sequence of SEQ ID NO:14.

Other fusion proteins may be obtained with the protein encoded in the gag gene or with a glycoproteins of a viruses, for example, other than a retrovirus, in particular a glycoprotein of VSV.

The invention also relates to a nucleotide sequence characterized in that it codes for a polypeptide described above.

Preferred nucleotide sequences are those which correspond to any one of the nucleotide sequences SEQ ID NO:15, NO:16, NO:17, NO:18, NO:19, NO:20 or to a sequence complementary to these sequences or also to a sequence capable of hybridizing with one of the above sequences under stringent conditions. Also included in the framework of the invention are the nucleotide RNA sequences which correspond to the nucleotide sequences described above.

The invention also relates to a recombinant cell host, characterized in that it includes a nucleotide sequence such as given above. Preferably the nucleotide sequence inserted in the cell host is integrated into the genome of this host. Different cell hosts may be selected for carrying out the invention according to the desired use. As examples it will be possible to use cell hosts such as bacteria, viruses or phages, insect or mammalian cells (COS, CHO), etc . . . for the study of molecules possibly exhibiting an affinity for the polypeptides of the invention.

A particularly preferred cell host is the MPLV virus. In particular, the invention relates to the MPLV virus containing in its genome a nucleotide sequence coding for the peptide represented by the sequence SEQ ID NO:2 in the form of a fusion protein with the viral glycoprotein gp70.

The invention also relates to recombinant vectors characterized in that they contain a nucleotide sequence such as described previously, inserted at a site inessential for replication under the control of regulatory sequences necessary for its expression in the specified cell host.

Particularly suitable vectors for carrying out the invention are, for example, the vaccinia virus or the baculovirus.

Also forming part of the invention are nucleotide probes consisting of at least 9 nucleotides and preferably 15 to 30 nucleotides, capable of hybridizing with a nucleotide sequence of the invention under stringent conditions, this probe being optionally labelled.

The probes used may be specific for the nucleotide sequences of the invention or unspecific for them when a sequence belonging to a larger group is studied.

Suitable markers for preparing the probes of the invention are standard radioactive markers or also enzymatic markers or any other appropriate marker.

Furthermore the invention relates to monoclonal or polyclonal antibodies, characterized in that they recognize one of the polypeptides according to the invention.

Particularly useful antibodies are directed against the extracellular domain of the polypeptide encoded in the c-mpl gene.

These antibodies are obtained according to the standard methods for producing antibodies. For the preparation of monoclonal antibodies in particular, recourse will be had to the method of Kohler and Milstein; in particular, monoclonal antibodies are prepared by cell fusion between myeloma cells and spleen cells of mice previously immunized with a polypeptide according to the invention, in conformity with the standard procedure.

The identification by the inventors of the polypeptide in the MPLV virus responsible for the myeloproliferative disease makes possible the development of agents for the in vitro detection of the abnormal expression of a polypeptide described in the preceding pages, revealing a pathological condition.

For this purpose the invention includes a procedure for the in vitro detection of the abnormal expression of a polypeptide of the invention, characterized in that it comprises: the placing of a biological sample likely to contain the desired polypeptide in contact with antibodies such as defined previously, the detection of an immunological reaction of the antigen-antibody type.

By "abnormal expression" of the polypeptide is meant any quantitatively abnormal expression, as well as any expression of a modified polypeptide whose function may be impaired.

Another procedure for the in vitro detection of the abnormal expression of a polypeptide of the invention may be performed by the in vitro detection of the abnormal expression of a nucleotide sequence coding for a peptide according to the invention. Such a procedure comprises:

a) the placing of a biological sample likely to contain the nucleotide sequence under investigation and to be used as a template in contact with a nucleotide primer capable of hybridizing with the nucleotide sequence under investigation in the presence of the 4 different nucleoside triphosphates and a polymerizing agent under hybridization conditions such that for each nucleotide sequence which has hybridized with a primer an elongation product of each primer is formed complementary to the template;

b) the separation of the template and the elongation product obtained, the latter then also being capable of acting as template;

c) the repetition of step a) so as to obtain a detectable amount of the desired nucleotide sequences;

d) the detection of the amplification product of the nucleotide sequences.

Details concerning the implementation of the PCR procedure are given for example in the patent applications EP 0200362 and EP 0229701.

The invention also relates to a kit for the in vitro detection of the abnormal expression of the polypeptides according to the invention, characterized in that it contains monoclonal or polyclonal antibodies capable of reacting with said polypeptide and, optionally, a reagent for the detection of the antigen-antibody immunological reaction.

Such a kit may be used for the performance of different types of assays, in particular RIA and ELISA assays.

The invention also relates to a procedure for the detection of the affinity of a molecule for a polypeptide according to the invention, characterized by:

the placing of the test molecule in contact with a cell host modified beforehand with a nucleotide sequence according to the invention under conditions allowing the expression of this sequence so as to obtain a polypeptide according to the invention bearing at least one site capable of interacting with the test molecule and exposed at the surface of the cell host, the detection of the formation of a complex between the test molecule and the polypeptide.

Furthermore the invention relates to a medicine characterized in that it contains a polypeptide complying with the preceding definitions in a soluble form, in combination with an acceptable pharmaceutical vehicle. Such a medicine can be used to remedy the abnormal production of the polypeptides of the invention in the cells of a patient.

The medicine according to the invention can act according to a competition reaction between the soluble form of a polypeptide present as an active ingredient in this medicine and the polypeptides present abnormally in the patient treated.

Other characteristics and advantages of the invention are presented in the examples which follow.

EXAMPLES

Molecular cloning of the MPLV provirus

The following experiments refer to the identification and characterization of the molecular rearrangements taking place at the envelope of the retrovirus MPLV.

Figure 1A:
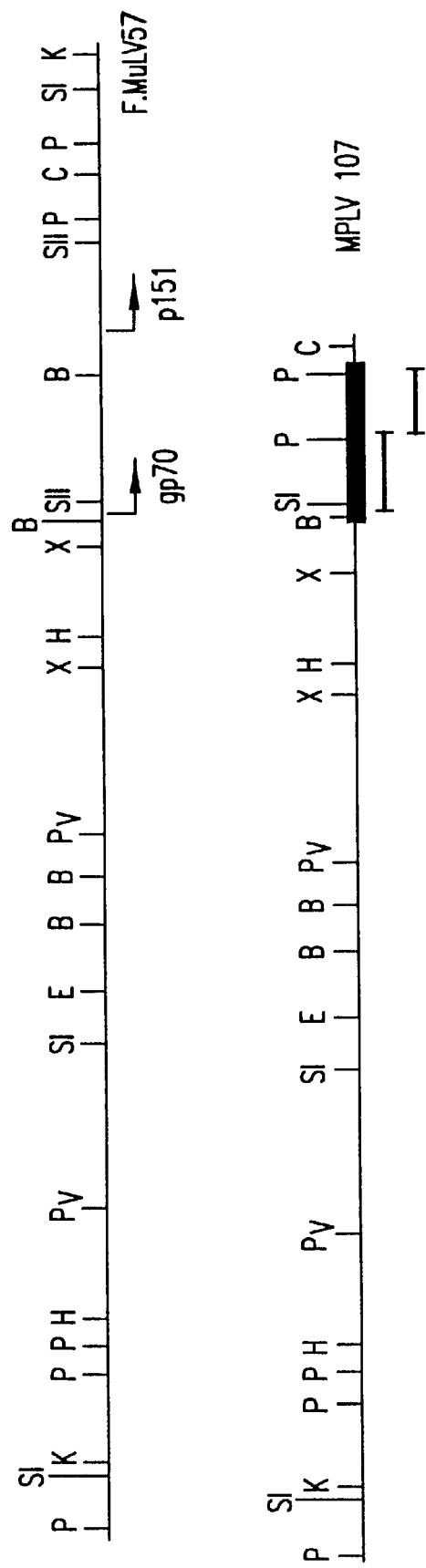
FIGS. 1A and B: (A) Restriction map of the clone MPLV 107 and clone F-MuLV 57 obtained by digestion with restriction endonucleases. The restriction sites for the following enzymes are designated as follows: B: BamHI, C:ClaI, E:EcoRI, H:HindIII, K:KpnI, P:PstI, Pv:PvuII, SI:SacI, SII:SacII, X:XbaI. The thick black line corresponds to the region specific to MPLV. The two probes derived from the MPLV envelope gene are shown by the thick black lines below the restriction map.
Figure 1B:
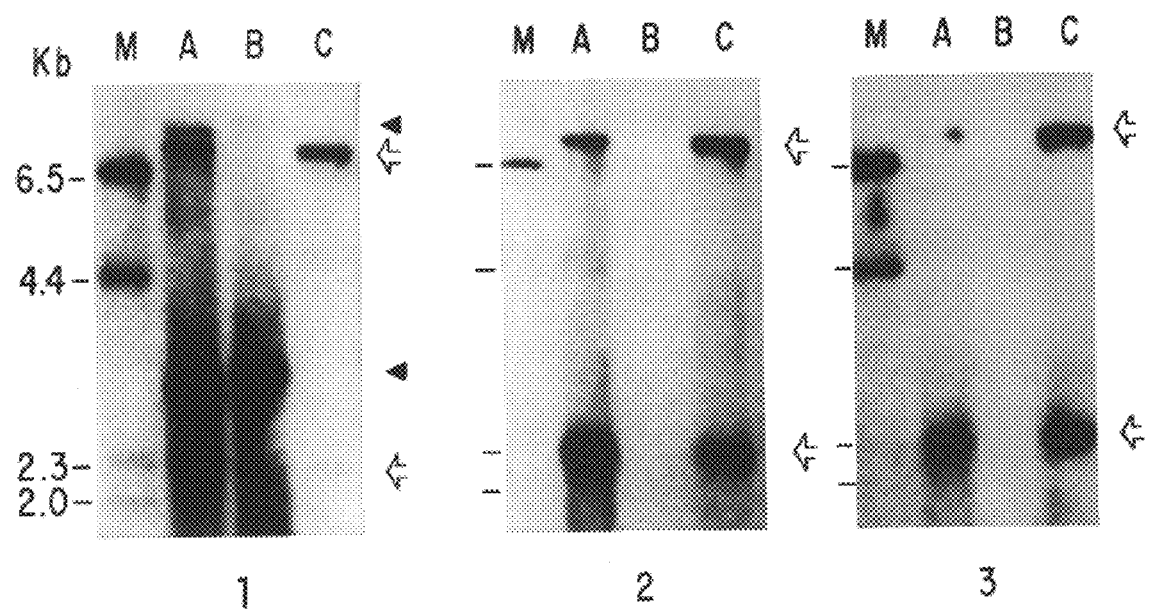

In order to characterize the rearranged region of the env gene, a cDNA library was prepared by using the RNA poly $A^+$ of the NIH 3T3 cells modified productively with the amphotropic pseudotype of MPLV. The cDNA clones comprising the complete env region of MPLV were obtained and two specific MPLV probes were prepared: they were the SacI-PstI and PstI-PstI fragments, each of 300 base pairs (FIG. 1A). The specificity of these two MPLV probes is shown in FIG. 1B, parts 1, 2 and 3. They recognize the genomic RNAs (7.4 kb) and the subgenomic RNAs obtained by splicing (2.4 kb) but do not hybridize with F-MuLV or with amphotropic RNAs.

In order to clone a biologically active MPLV provirus, a genomic library was prepared from non-producing *Mus dunni* cell clones containing a single copy of the MPLV provirus (Penciolelli et al.,1987). Of the $1.5 \times 10^6$ recombinant phages screened with the two specific MPLV probes, a single clone was obtained (MPLV 107). Restriction analyses have shown that this clone contains the complete genome of MPLV with the exception of the LTR 3' part (FIG. 1A).

In order to demonstrate that this molecular entity was responsible for the characteristics of the acute myeloproliferative disease caused by MPLV, a complete provirus was constructed by ligation of MPLV 107 to the clone F-MuLV 57 3' LTR. The resulting construction (MPLV3) was cotransfected with the DNA of the auxiliary virus F-MuLV into the NIH 3T3 cells in a molar ratio of 10/1 (MPLV3/F-MuLV). After several cell passages, the viral supernatant was injected intravenously into young adult D BA/2 mice known for their resistance to early erythroleukemia induced by F-MuLV (Ruscetti et al., 1981, J.Exp. Med. 154, 907–920).

The animals inoculated with the supernatant of the cultures transfected with the DNA of F-MuLV alone were healthy6 months after infection. On the other hand, all of the mice inoculated with the supernatant of the cultures transfected with the DNAs of MPLV3 and F-MuLV rapidly developed splenomegaly, hyperleukocytosis and polycythemia and were dead two months after the inoculation. The progenitor cells of the sick animals were then examined in vitro in order to determine their needs in terms of hematopoietic growth factors. 100% of the late progenitor cells of the red cells (erythroid colony forming units) formed hemoglobinised erythrocyte colonies without the addition of erythropoietin (EPO) whereas 62% of the cells forming the CFU-C colonies in the spleen and 30% of the CFU-C in the bone marrow proliferated and differentiated without the exogenous addition of factors which stimulate the colonies. They led to mature colonies of granulocytes, monocytes, megacaryocytes, erythrocytes and to multipotent colonies containing different cell lines.

Thus the clone MPLV3 was biologically active and its properties could not be distinguished from those of the original MPLV isolate.

Sequence and structure of the env region of MPLV

The rearranged env genes of the cDNAs of MPLV and of the genomic clone were sequenced and proved to be identical. The nucleotide sequence was analysed showing that the env gene of MPLV comprises sequences derived from the env gene of F-MuLV and non-viral sequences. As is illustrated in FIG. 2A two deletions have appeared in the env gene of F-MuLV: the first between the positions 5969 and 6505 and the second between the positions 6615 and 7513 (Koch et al., 1983, J. Virol. 45, 1–9). The env gene of MPLV is thus a complex region composed between the 5' and 3' ends of 191 base pairs of the 5' end of the env gene of F-MuLV (up to position 5969) followed by 110 base pairs of the central region of the env gene of F-MuLV (between the positions 6506 and 6615), then by a non-viral region of 623 nucleotides and finally the 3' part of the 15E protein of F-MuLV (starting from position 7513).

Figure 2B:
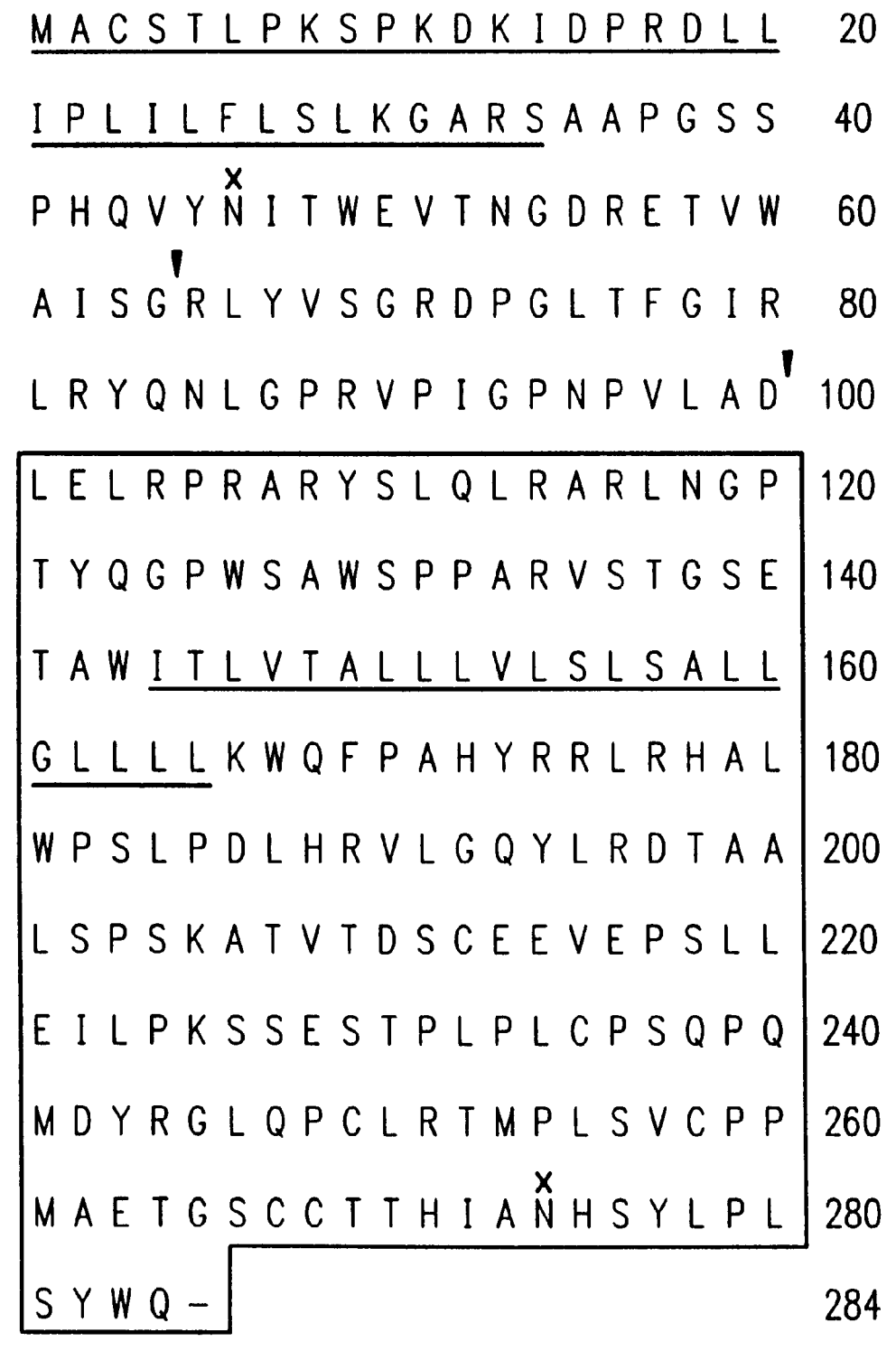

The env gene of MPLV has an open reading frame of 284 amino acids starting from the initiation codon ATG of gp70 and terminating at the stop codon TAG within the sequence specific for MPLV (FIG. 2B) and codes potentially for an env fusion protein with a molecular weight of 31 kilodaltons. This env-vmpl fusion protein comprises 64 amino acids of the $NH_2$-terminal part of the gp70 of F-MuLV including the signal peptide, 36 amino acids of the central region of the env gene of F-MuLV and 184 amino acids specific to MPLV.

A hydrophobicity curve (Kyte et at., 1982, J. Mol. Biol. 157, 105–132) of the amino acid sequence of the product of the env gene of MPLV revealed, in addition to the 34 hydrophobic amino acids of the signal peptide of the gp70, that the domain specific to MPLV contains a region of 22 uncharged amino acids extending from the amino acid Ile at position 143 to the amino acid Leu at position 165, which may correspond to a membrane domain. The natural env protein of MPLV would thus be constituted of an extracellular domain of 109 amino acids with a potential glycosylation site, a transmembrane domain of 22 amino acids and an intracytoplasmic domain of 119 amino acids without a sequence for a kinase activity (Hanks et al., 1988, Science vol. 241, p.42–52).

A search of the EMBL data (nucleic acid and proteins) showed that the sequence specific for MPLV, designated by v-mpl, does not correspond to a gene identified up to now.

env region of MPLV containing a unique highly conserved cell sequence in mammals The presence of a possible c-mpl locus in the mouse, rat, mink, cow, dog and in humans was investigated. The hybridization of the DNA digested by EcoRI with the two RNA probes of v-mpl led to the detection of clear-cut bands under stringent conditions of hybridization, indicating the presence of a cellular counterpart (c-mpl) to the v-mpl sequence in the 6 species tested (FIG. 3).

The expression of c-mpl was then investigated in different tissues of the mouse. Northern blots of RNA poly $A^+$ prepared from fetal liver and from different organs of the adult mouse hybridized with v-mpl RNA probes. As is shown in FIG. 4 a single band of mRNA of 3.0 kb could be detected in the adult spleen (lane 4) and in fetal liver (line 8). A similar transcript was also present in the bone marrow. On the other hand, no transcript was detected in the brain, liver, salivary glands, kidney, testicles or thymus of adult mice.

The leukemogenic properties of MPLV can thus be attributed to the presence of a novel oncogene, v-mpl, transduced from cellular sequences conserved in the phylogeny of the mammals and transcribed in normal mouse hematopoietic tissues.

MPLV transforms hematopoietic progeny in vitro

In order to determine whether MPLV could directly transform hematopoietic cells and in order to analyse the nature of the target cells of the virus, bone marrow cells were infected in vitro with MPLV uncontaminated with auxiliary virus, obtained in a packaging cell line psi-CRE (Danos and Mulligan, 1988, P.N.A.S. USA 85, 6460–6464). The test was carried out in an agarose medium with a low concentration of cells in order to avoid stimulating the formation of colonies by endogenous factors secreted by helper cells. In repeated experiments only a few autonomous colonies were detected. However, when the infection was carried out with bone marrow cells enriched in immature progenitor cells induced to divide by a pretreatment of the mice with 5-fluorouracil (5-FU) (Hodgson and Bradley, 1979, Nature vol. 281, p. 381–382) colonies developed spontaneously in significant numbers. About half were colonies of a single line such as colonies of megacaryocytes or granulocytes or erythroid colonies. The other colonies were mixed colonies, about 20% of which represented three or more lines of differentiation. Subculturing experiments of colonies containing one or two lines of differentiation did not lead to the production of secondary colonies which indicates that these colonies resulted from progeny irreversibly committed to differentiation. On the other hand, more than 65% of the colonies containing several lines of differentiation (12/18) produced a variable number of secondary colonies (from 7 to 286) expressing one or two lines of differentiation but also macroscopic colonies in which at least three lines were present. Some of these colonies (3/18) produced mixed tertiary colonies. This indicates that MPLV is capable of promoting the proliferation and the terminal differentiation of both multipotent cell strains and progenitor cells already committed to differentiation.

MPLV immortalizes bone marrow cells in culture and induces their differentiation When bone marrow cells infected by MPLV and obtained from normal mice or mice pretreated with 5-FU are placed in culture, a 10 to 20 fold increase in the percentage of the frequency of progenitor cells was observed in the same time as an increase in the percentage of colonies independent of growth factors. The growth of such cultures is shown in FIG. 5. Whereas cells in the uninfected cultures the had low growth, the cells infected by MPLV contained non-adhesive cells which divided rapidly and which may be transferred to new flasks lacking adhesive nurse stromal cells. The cells continued to proliferate by forming permanent cell lines growing in suspension and containing erythroblasts in the terminal phase of differentiation, megacaryocytes and polymorphonuclear leukocytes in association with immature blast cells. When these cells are cultivated on semi-solid medium, different types of autonomous colonies containing mature cells develop.

Four to six weeks after infection the majority of the cell lines developed towards a more restricted phenotype which appeared to remain stable for months in continuous culture. A morphological examination of the cells in suspension and of the colonies obtained on a semi-solid medium has shown that, of the 24 lines, one line remained multipotent, five contained mature megacaryocytes and hemoglobinized erythroblasts, five were composed of megacaryocytic cells, five were mastocytes, four of the myelomonocytic cells, two contained erythroblastic cells in the process of differentiation and two corresponded to immature blast cells. Experiments were carried out to determine whether these cultures were of the monoclonal or polyclonal type. The result obtained was that these permanent cell lines are obtained starting from the growth of a single or a few multipotent strains infected by MPLV, in which the restriction of the capacities of differentiation occurs at a later stage. The malignant character of the cell lines was demonstrated by subcutaneously injecting $2 \times 10^6$ cells into syngenic mice irradiated with a sublethal dose (5 Gy) of radiation or into nude mice. A tumor did not develop at the site of inoculation when the cells obtained from a less than 4 months' old culture were injected but 6 of the 10 cell lines inoculated after more than 7 months produced hematopoietic tumors of the nature of those cell lines injected after a latency period of about 30 days.

In order to investigate whether the autonomous growth of the cells resulted from the production of a growth factor, supplemented media for different cell lines, concentrated 10 times, were tested on the indicator cell line FDC-P1 (Dexter et al., 1980, J. Exp. Med. 152, 1036–1047). No incorporation of $^3H$ thymidine could be detected. Continuous growth was thus not sustained by the secretion of IL3 or GM-CSF. In addition, Northern blot analyses did not reveal the mRNA of IL3, GM-CSF, G-CSF or EPO in twelve cell lines examined except in the case of one cell line which expressed GM-CSF mRNA.

Thus, these observations indicate that MPLV alone is capable of directly transforming multipotential hematopoietic progenitors committed to differentiation and leads to the rapid emergence of different immortalized cell lines independent of growth factors which maintain the capacity to differentiate spontaneously.

The experiments previously described have shown that the pathogenicity of MPLV was not due to major modifications in its LTR part. The analysis of the sequence of the env region of MPLV showed that the env gene of MPLV did not contain sequences related to sequences of the MCF virus but that one sequence of 1.5 kb of the envelope of F-MuLV was deleted and replaced by a novel non-viral sequence of 0.7 kb which did not exhibit homology with known genes. This novel sequence, v-mpl, is of cellular origin and is conserved among the mammals including man. The proto-oncogenic c-mpl is transcribed in the form of an mRNA 3.0 kb in the spleen of the adult mouse and in the bone marrow and in the fetal liver. c-mpl is located on chromosome 4 of the mouse and on human chromosome 1-p34.

The polypeptide env-mpl exhibits the general characteristics of a transmembrane protein: it contains the signal peptide of gp70 at its N-terminus and a unique transmembrane domain, indicating that the N-terminal part of the molecule is extracellular and the C-terminal part is intracellular. The amino acid sequence of the extracellular domain of the v-mpl protein exhibits similarities to the hematopoietic receptors of the cytokines recently cloned such as the beta chain of IL2R, IL3R, IL4R, IL6R, IL7R, GM-CSFR, G-CFSR, EPO-R, as it does to the prolactin receptor. Thus this sequence contains a motif W S X W S in the extracellular domain close to the transmembrane region and does not contain a consensus sequence for a protein kinase activity in the intracytoplasmic domain. It has also been observed that the cytoplasmic domain of v-mpl contains many proline (14/119, 12%) and serine (13/119, 11%) residues, as is the case for other receptors. The result is that MPLV has transduced a truncated form of a receptor for a hematopoietic growth factor. The expression of the endogenous c-mpl gene observed uniquely in spleen cells, the bone marrow and fetal liver confirms this hypothesis.

EXPERIMENTAL PROCEDURES

Cells, viruses and mice

NIH 3T3 and *Mus dunni* cells were used. The isolation of the clone 2 of *Mus dunni*, a non-producer of MPLV, was described in the publication by Penciolelli et al., 1987 (J. Virol. 61, 579–583). The amphotropic MPLV pseudotype was obtained in superinfecting clone 2 of *Mus dunni* with the amphotropic helper virus 4070A (Chattopadhyay et al., 1981; J. Virol. 39, 777–791).

DBA/2J, C57BL/6J and nude mice were obtained from Iffa Credo (l'Arbesle, France) and reared under pathogen-free conditions. Six to eight week old animals were used in all of the experiments.

Preparation of the RNA and Northern blot analysis

The total RNA was purified according to the guanidium thiocyanate/CsCl method (Chirgwin et al., 1979; Biochemistry 18, 5294–5299) and the RNA poly $A^+$ were selected by chromatography on an oligo dT-cellulose column.

In the case of the Northern blot analysis, 5 ug poly $A^+$ RNA was were denatured in a glyoxal buffer according to McMaster and Carmichael, 1977 (Proc. Natl. Acad. Sci. USA 74, 4835–4838). The electrophoresis was carried out in 1.1% agarose gels in 10 mM $Na/Na_2$ phosphate buffer. The RNA transfers were carried out on nitrocellulose Hybond C-extra (Amersham) as described by Thomas, 1980 (Proc. Natl. Acad. Sci. USA 77, 5201–5205). The membranes were prehybridized for 5 hours at 55° C. in 50% formamide, 4×SSC, 0.05M $Na/Na_2$ phosphate, 1× Denhardt, 500 μg/ml yeast tRNA and 250 μg/ml of herring sperm DNA. $10^7$ cpm of an RNA probe labelled with $^{32}P$ were added and hybridization was carried out for 40 hours at 55° C. The membranes were washed twice for 5 minutes at room temperature in 2×SSC–0.1% SDS, twice for 30 minutes at 65° C. in 2×SSC–0.1% SDS and twice for 30 minutes at 65° C. in 0.1×SSC–0.1% SDS.

Southern blot analysis

The DNAs were digested with suitable restriction endonucleases under the conditions indicated by the manufacturer and loaded on to a 0.8% agarose gel. After electrophoresis, the DNAs were transferred to nitrocellulose membranes according to the method of Southern (1975; J. Mol. Biol. 98, 503–518). The membranes were hybridized with $10^7$ cpm of probes labelled with $^{32}P$ under conditions described for Northern blot.

Construction of the cDNA library for the MPLV envelope

The cDNA was synthesized from the poly $A^+$ RNA prepared from NIH 3T3 cells in the exponential phase of growth, productively infected with MPLV pseudotyped by the helper amphotropic virus 4070 A (MPLV comprising the envelope of the 4070 A virus) by using the Amersham kit of synthetic cDNAs. Blunted ended cDNAs were ligated to a dephosphorylated vector pSPT18 digested with SmaI in the presence of T4 DNA ligase.

Competent LM 1035 bacteria were transformed and spread on agar plates containing ampicillin. The colonies containing the recombinant plasmids were transferred to nitrocellulose filters. The identification of the clones containing the cDNA for the envelope (env) of MPLV was performed by in situ hybridization as described by Sambrook et al., 1989 (Cold Spring Harbor Laboratory Press), with a probe E57BS (Moreau-Gachelin et al., 1983 Biochimie 65, 259–266), labelled with $^{32}P$ by means of the "nick-translation" procedure.

Construction of the genomic library of MPLV

High molecular weight DNA was extracted according to Souyri et al., 1983 (Proc. Natl. Acad. Sci. USA 80, 6676–6679) from clone 2 of Mus dunni, a non-producer of MPLV, and partially digested with the restriction endonuclease Sau3A. The DNA fragments (10 to 15 kb) were purified by means of centrifugation on a sucrose gradient and ligated with BamHI arms of the bacteriophage EMBL3 after encapsidation (Stratagene). After in vitro encapsulation (Gigapack, Stratagene), the recombinant phages containing the DNA of MPLV were identified according to the procedure of Benton et al., 1977 (Science 196, 180–182) by hybridization with RNA probes specific for MPLV. The filters were prehybridized for 5 hours at 42° C. in 50% formamide, 5×SSC, 5× Denhardt, 0.1% SDS, 50 mM of $Na/Na_2$ phosphate pH 6.5 and 250 μg/ml of herring sperm (2 ml per filter). The hybridization with RNA probes of MPLV, labelled with $^{32}P$ was performed for 20 hours at 42° C. in 50% formamide, 5×SSC, 1× Denhardt, 0,1% SDS, 50 mM of $Na/Na_2$ phosphate pH 6.5 and 250 μg/ml of herring sperm (1 ml of buffer and $2\times10^6$ cpm of RNA probe per filter). The filters were washed twice for 10 minutes at room temperature in 2×SSC–0.1% SDS, 30 minutes with 2×SSC–0.1% SDS, and twice for 30 minutes with 0.2×SSC–0.1% SDS, each time at 65° C.

Sequencing of the DNA

The sequencing of DNA was performed by using the dideoxy chain termination method (Sanger et al., 1977; Proc. Natl. Acad. Sci. USA 74, 5463–5467) modified for use with the T7 DNA polymerase (Sequenase USB). The samples were denatured for 2 minutes at 75° C. and loaded on to a denaturing acrylamide gel (6% acrylamide, 8M urea, 1×TBE).

The analysis of sequences, and the comparison of the nucleotide and protein sequences between mpl and the genes included in the EMBL library were made by using the FASTP programmes (Lipman et al., 1985; Science 227, 143–1441) and PC-GENE (Intelligenetics Inc. and Genofit SA).

In vitro Infection of hematopoietic cells and establishment of cell lines

Cell clones producing MPLV but lacking a helper virus were obtained by cotransfection of psi-CRE packaging cells with the plasmid pSV2 Neo and about a 10-fold excess of the plasmid pMPLV3. After selection and isolation of clones resistant to G418 (Gibco BRL), the clones producing MPLV were selected by blotting the whole cells according to Wendling et al., 1989 (Leukemia 3, 475–480). The blots of the virus purified from the supernatants were used to select a clone producing a high titer of virus. 5 million normal bone marrow cells or $1.5\times10^6$ cells of adult male C57BL/6 mice pretreated with 5-fluorouracil (150 mg/kg body weight, 4 days before) were suspended in 1 ml of infectious supernatant. The incubation was performed for 2 hours at 37° C. in an atmosphere containing 5% $CO_2$ in air. The cells were then placed on a semi-solid medium or cultivated at a concentration of $2.5\times10^6$ cells/ml in 25 $cm^2$ culture flasks containing 8 ml of Dulbecco medium modified according to Iscove (IMDM) supplemented with 20% of heat-inactivated fetal calf serum (Flow Laboratories). After 10 to 12 days non-adhesive cells were recovered and transferred at a concentration of $2.5\times10^5$ cells/ml into new flasks containing fresh medium. The cells were then passed every 4 to 7 days or more frequently, depending on the extent of cell growth.

Tests on the progenitor cells

In the case of the CFU-E colonies, the cells were inoculated in a plasma coagulum culture system such as that described by McLeod et al., 1978 (M. J. Murphy, ed-springer Verlag, New York—pp 31–35). A suitable number of cells was distributed in a volume of 0.1 ml with or without 0.25 U/ml Epo (erythropoietin) (Stage 1 human EPO, specific activity 1000 U/mg; Terry Fox Laboratory, Vancouver, Canada). The cultures were harvested on day 2. The colonies containing at least 8 erythroblasts positive to benzidine were listed as CFU-E colonies.

In the case of the CFU-C colonies the tests were performed in 0.5 ml of agarose (Seaplaque agarose, FMC) in cultures on Linbro plates (CT-CV 96) according the method of McLeod et al., 1978, previously mentioned. In the case of the control cultures, the formation of colonies was stimulated maximally by the addition of 5% (vol./vol.) of a supplemented medium prepared from spleen cells stimulated with a mitogen (PWMSCM) and 1 U/ml Epo. The cultures were incubated in an atmosphere of saturating humidity containing 5% $CO_2$. After incubation for 7 days, the cultures were withdrawn from the wells, placed on glass slides and fixed in phosphate buffer containing 5% glutaraldehyde (pH 7), stained with either benzidine, myeloperoxidase or acetyl cholinesterase, then with hematoxylin to determine the cellular composition of each colony.

We claim:

1. An isolated polypeptide comprising the amino acid sequence of SEQ ID NO:1.

2. An isolated nucleic acid molecule comprising a nucleotide sequence encoding the polypeptide according to claim 1.

3. A recombinant host cell containing the nucleic acid molecule according to claim 2, which nucleic acid molecule is recombinant.

4. The recombinant host cell according to claim 3, wherein said host cell is a mammalian host cell.

5. The recombinant host cell according to claim 4, wherein said mammalian host cell is a COS cell or CHO cell.

6. The recombinant host cell according to claim 3, wherein said host cell is an insect host cell.

7. The nucleic acid molecule according to claim 2 that is a recombinant vector wherein the nucleotide sequence is under the control of regulatory sequences necessary for the expression of said nucleotide sequence in a host cell.

8. The recombinant vector according to claim 7, wherein said vector is obtained from a baculovirus.

9. The recombinant vector according to claim 7, wherein said vector is a virus.

10. The recombinant vector according to claim 9, wherein said virus is MPLV.

11. An isolated polypeptide comprising an amino acid sequence selected from the group consisting of SEQ ID NO:7, and SEQ ID NO:12.

12. An isolated nucleic acid molecule comprising a nucleotide sequence selected from the group consisting of SEQ ID NO:15 and a sequence complementary to SEQ ID NO:15.

13. A composition comprising a polypeptide comprising an amino acid sequence selected from the group consisting of SEQ ID NO:1, SEQ ID NO:7, and SEQ ID NO:12, in combination with an acceptable pharmaceutical vehicle.

14. A fusion protein comprising a first polypeptide having an amino acid sequence selected from the group consisting of SEQ ID NO:1, SEQ ID NO:7 and SEQ ID NO:12 and a second polypeptide having the amino acid sequence of gp70 of MPLV.

15. An isolated polypeptide comprising a fragment of a polypeptide, which polypeptide has the amino acid sequence of SEQ ID NO:1, said fragment being soluble, and said fragment having an amino acid sequence selected from the group consisting of SEQ ID NO:7 and SEQ ID NO:12.

16. An isolated first nucleic acid molecule which is hybridizable under highly stringent conditions to the complement of a second nucleic acid molecule having the nucleotide sequence of SEQ ID NO:15, said first nucleic acid encoding a polypeptide which meets at least one of the following conditions:

(a) when said polypeptide is produced from the genome of the retrovirus MPLV, it causes the proliferation of megacaryocytic cell lines in vitro and in vivo;

(b) said polypeptide promotes cellular differentiation of megacaryocytic cell lines, when it is produced from the genome of the retrovirus MPLV; or (c) said polypeptide reacts in vivo as a receptor for a megakaryocytic growth factor, either at the level of ligand binding or at the level of signal transmission.

17. An isolated polypeptide encoded by the first nucleic acid molecule of claim 16.

* * * * *

UNITED STATES PATENT AND TRADEMARK OFFICE
CERTIFICATE OF CORRECTION

PATENT NO.   : 5,925,750

DATED        : July 20, 1999

INVENTOR(S)  : Charon et al.

It is certified that error appears in the above-identified patent and that said Letters Patent is hereby corrected as shown below:

Please correct the name of Assignee to read: -- Institut National de la Santé et de la Recherche Médicale --.

Signed and Sealed this

Twenty-ninth Day of May, 2001

Attest:

NICHOLAS P. GODICI

*Attesting Officer*        *Acting Director of the United States Patent and Trademark Office*